(12) United States Patent
Laird et al.

(10) Patent No.: US 10,345,283 B1
(45) Date of Patent: Jul. 9, 2019

(54) SOIL NITRATE SENSING SYSTEM FOR PRECISION MANAGEMENT OF NITROGEN FERTILIZER APPLICATIONS

(71) Applicant: Iowa State University Research Foundation, Inc., Ames, IA (US)

(72) Inventors: David Laird, Nevada, IA (US); Natalia Rogovska, Ames, IA (US); Chien-Ping Chiou, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 135 days.

(21) Appl. No.: 15/372,066

(22) Filed: Dec. 7, 2016

Related U.S. Application Data

(60) Provisional application No. 62/263,788, filed on Dec. 7, 2015.

(51) Int. Cl.
| | | |
|---|---|---|
| *G01N 33/24* | (2006.01) | |
| *C05C 11/00* | (2006.01) | |
| *G01N 21/552* | (2014.01) | |
| *G01N 21/3563* | (2014.01) | |
| *G01N 21/35* | (2014.01) | |

(52) U.S. Cl.
CPC .............. *G01N 33/24* (2013.01); *C05C 11/00* (2013.01); *G01N 21/3563* (2013.01); *G01N 21/552* (2013.01); *G01N 2033/245* (2013.01)

(58) Field of Classification Search
CPC .... G01N 33/24; G01N 33/00; G01N 21/3563; G01N 21/35; G01N 21/25; G01N 21/17; C05C 11/00

USPC ................................................. 436/110, 106
See application file for complete search history.

(56) References Cited

U.S. PATENT DOCUMENTS

| | | | | |
|---|---|---|---|---|
| 5,033,397 | A * | 7/1991 | Colburn, Jr. ......... | A01B 79/005 111/118 |
| 8,204,689 | B2 | 6/2012 | Christy et al. | |
| 8,290,375 | B2 | 10/2012 | Szafraniec et al. | |
| 8,472,023 | B2 * | 6/2013 | Preiner ................ | G01N 21/276 356/432 |
| 8,933,406 | B2 | 1/2015 | Ressler et al. | |

OTHER PUBLICATIONS

Pons, A High-Tech Look at Soil Composition, http:www.usda.gov, Oct. 9, 2002, pp. 1-4, obtained by Examiner on Sep. 7, 2018. (Year: 2002).*

(Continued)

*Primary Examiner* — Christine T Mui
(74) *Attorney, Agent, or Firm* — McKee, Voorhees & Sease, PLC

(57) ABSTRACT

An apparatus, method, and system for on-the-go soil nitrate level sensing, and optionally using the sensing to inform or instruct nitrogen fertilizer application across the field. In one form, the apparatus includes a soil sensing tool which carries a diamond ATR cell in combination with an FTIR field ruggedized spectrometer. The optical surface of the diamond ATR cell can be adjusted in pitch and depth to the soil. A processor is programmed to manipulate acquired spectra to derive a prediction of nitrate level for a given soil position in the field. This can be used to modulate a fertilizer applicator operation or coupled with georeference data collected simultaneously to generate a map of soil nitrate levels for the field, which can be used as a prescription for nitrogen fertilizer application.

22 Claims, 25 Drawing Sheets

(56) References Cited

OTHER PUBLICATIONS

Blackmer, A.M., et al. "Correlations between Soil Nitrate Concentrations in Late Spring and Corn Yields in Iowa" J. Prod. Agric. (1989) vol. 2, No. 2, pp. 103-109.
Magdoff, Fred, "Understanding the Magdoff Pre-Sidedress Nitrate Test for Corn", J. Prod. Agric. (1991) vol. 4, No. 3, pp. 297-305.
Jaynes, D.B., et al. "Using the Late Spring Nitrate Test to Reduce Nitrate Loss within a Watershed", J. Environ. Qual. (2004) 33: pp. 669-677.
Christy, Colin D., et al. "An On-The-Go Spectral Reflectance Sensor for Soil" Presentation for 2003 ASAE Annual International Meeting, Jul. 27-30, 2003, 7 pages.
Linker, Raphael, et al. "Fourier Transform Infrared-Attenuated Total Reflection Nitrate Determination of Soil Pastes Using Principal Component Regression, Partial Least Squares, and Cross-Correlation", Society for Applied Spectroscopy (2004) vol. 58, No. 5, pp. 516-520.
Linker, Raphael, et al. "Soil Identification and Chemometrics for Direct Determination of Nitrate in Soils Using FTIR-ATR Mid-Infrared Spectroscopy" Chemosphere (2005) 61: pp. 652-658.
Linker, Raphael, et al. "Nitrate Determination in Soil Pastes Using Attenuated Total Reflectance Mid-Infrared Spectroscopy: Improved Accuracy via Soil Identification" Biosystems Engineering (2006) 94(1) pp. 111-118.
Agilent 4100 Exoscan Product Literature, 69 pages.
Chang, Cheng-Wen, et al. "Near-Infrared Reflectance Spectroscopy-Principal Components Regression Analyses of Soil Properties" Soil Sci. Soc. Am J. (2001) 65: pp. 480-490.
Chang, Cheng-Wang, et al. "Near-Infrared Reflectance Spectroscopic Analysis of Soil C and N" Soil Science (2002) vol. 167, No. 2.
FT-IR Spectroscopy, Attenuated Total Reflectance ATR, Pike Technologies, 24 pages, Retrieved from the internet Nov. 9, 2015.
DuPont Pioneer, Crop Focus, "Nitrogen Fertilizers and Stabilizers for Corn Production" product description, 2 pages, Retrieved from the Internet Nov. 9, 2016.
Yara International, "Field Applied Nitrogen Fertilizer" product description from website: www.yara.com/products, 1 page, copyright 2013.
American Society of Agronomy, 2016 Meeting, Poster Presentation, 1 page, Retrieved from the internet Nov. 19, 2016.

\* cited by examiner

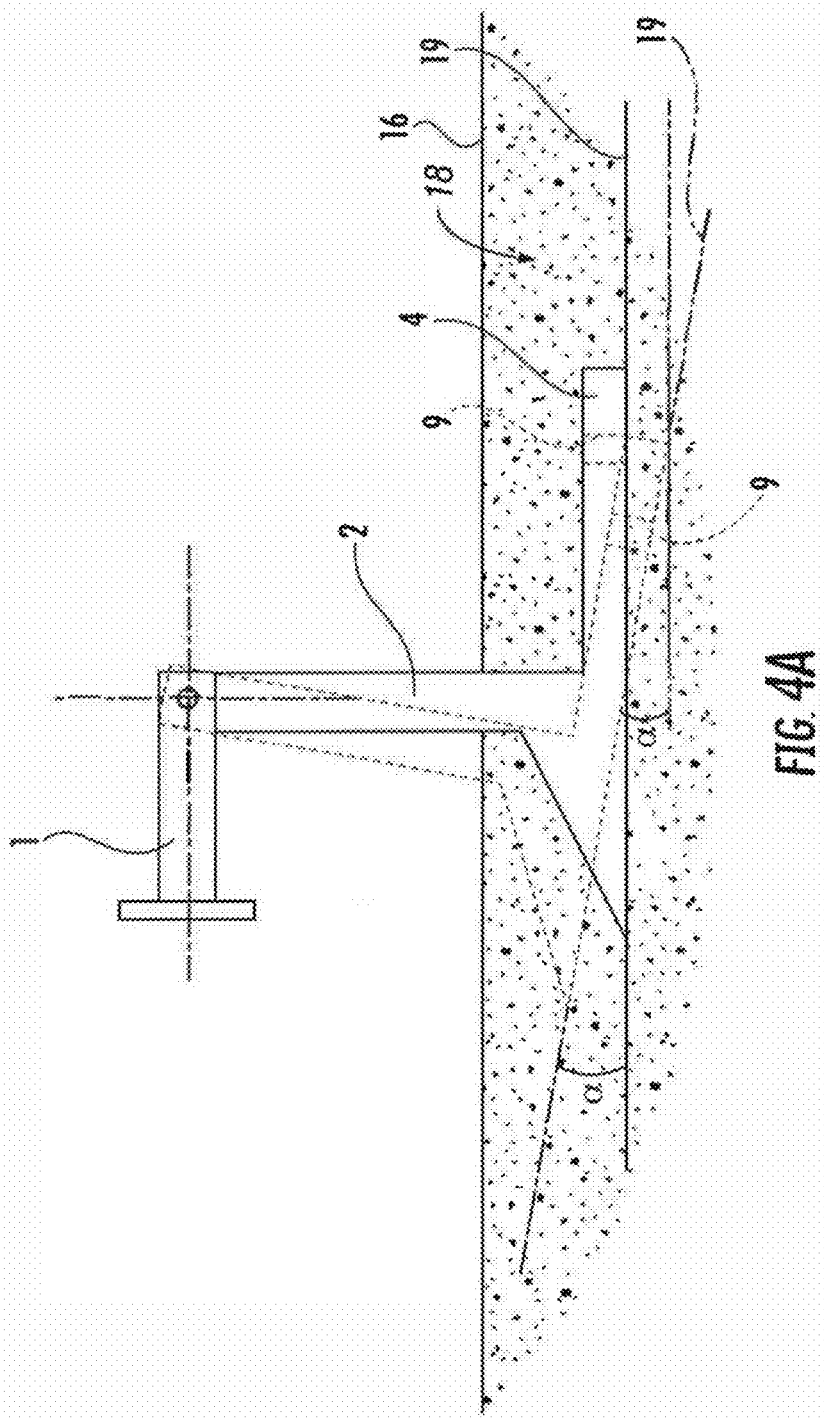

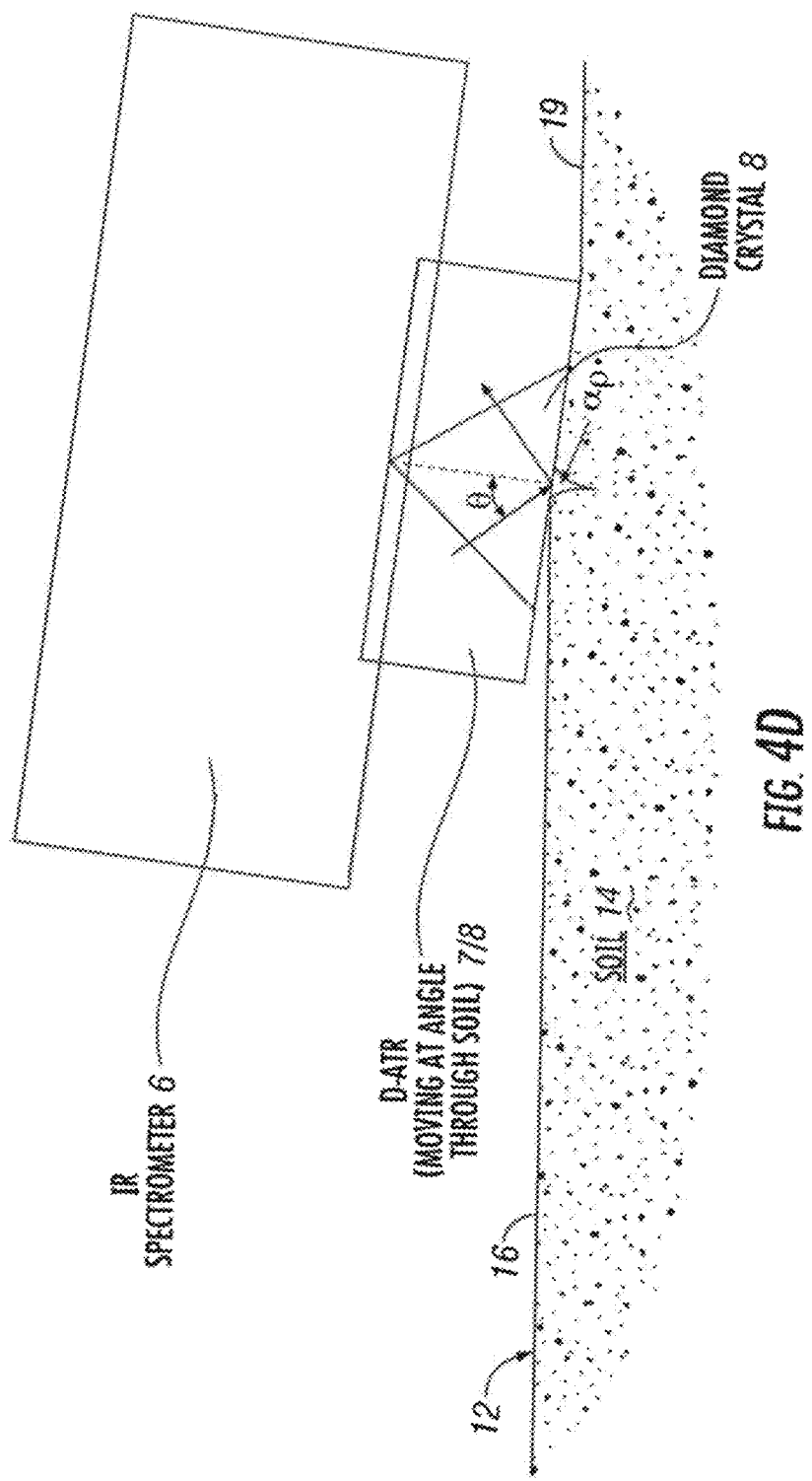

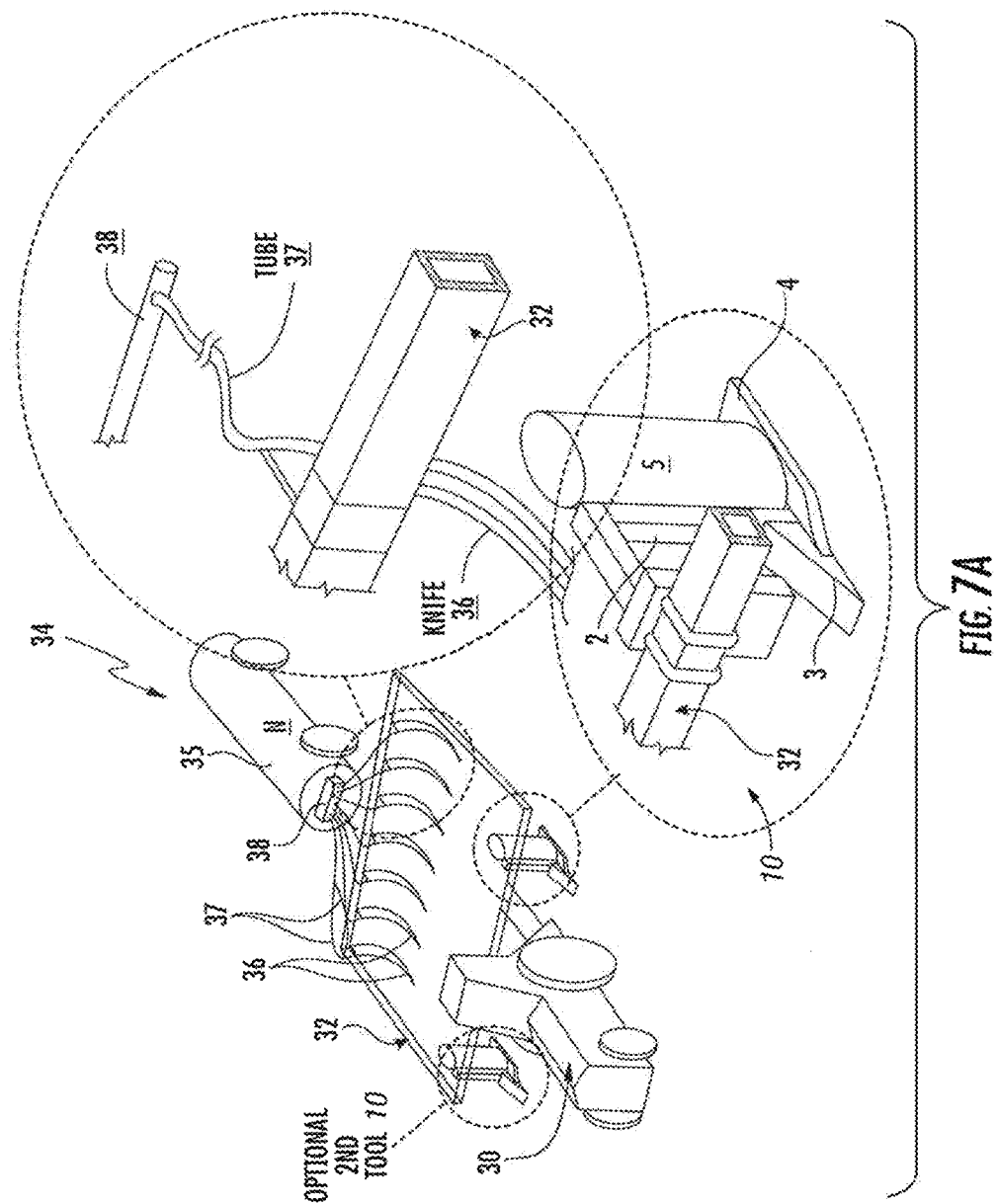

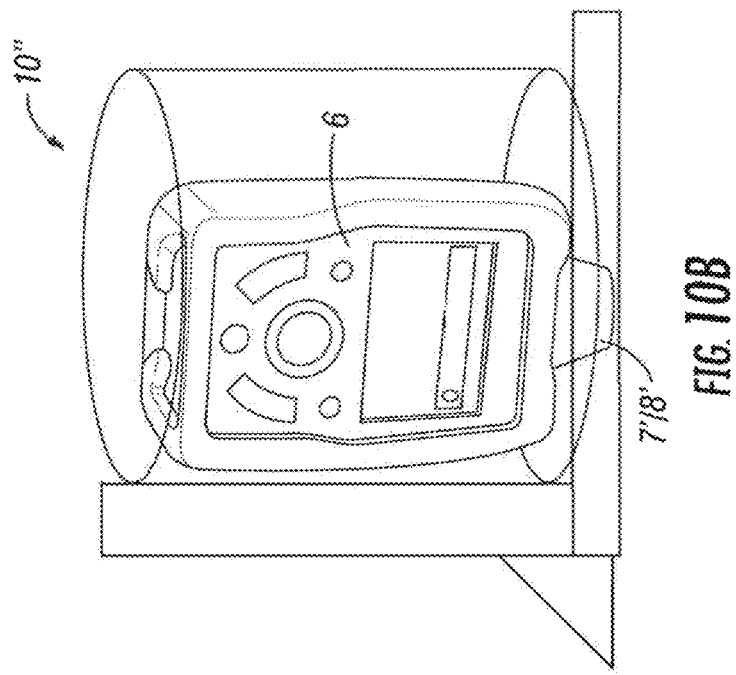
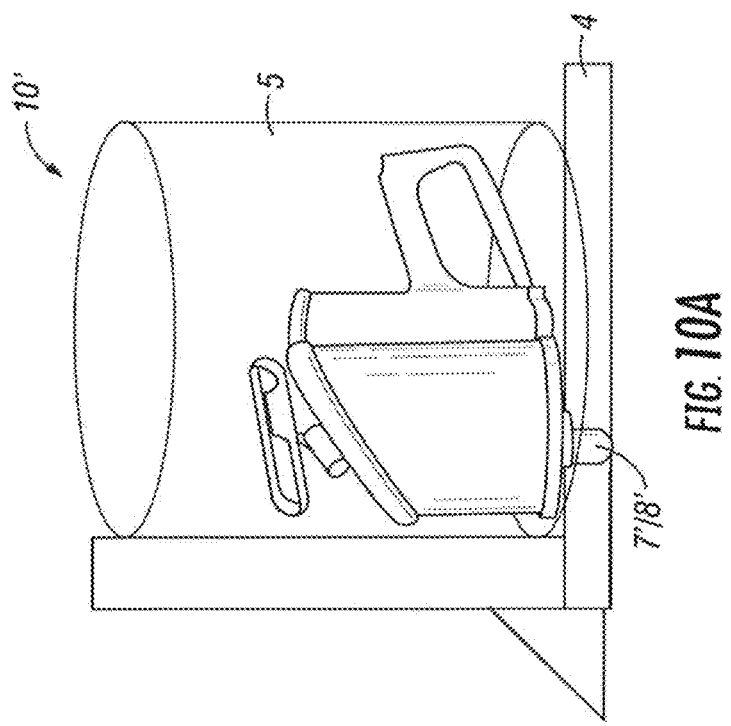

Relationship between measured and predicted soil $NO_3^-$ concentrations pooled for five soil types.

SOIL NITRATE SENSING SYSTEM FOR PRECISION MANAGEMENT OF NITROGEN FERTILIZER APPLICATIONS

CROSS-REFERENCE TO RELATED APPLICATIONS

This application claims priority under 35 U.S.C. § 119 to provisional application Ser. No. 62/263,788 filed Dec. 7, 2015, herein incorporated by reference in its entirety.

BACKGROUND OF THE INVENTION

Field of the Invention

The present invention relates to tools for agriculture and, in particular, to methods, systems, and apparatus to efficiently determine soil nitrate levels across a crop field to inform efficient use of nitrogen fertilizer (N fertilizer) across the field.

Problems in the State of the Art

Background:

Less than 50% of the 5 M tons of nitrogen (N) fertilizer that is applied on the 92 M acres of maize grown in the U.S. annually is actually used by crops; the rest is lost to the atmosphere as ozone causing $NO_x$, $NH_3$, and the potent greenhouse gas $N_2O$, or lost to leaching as $NO_3^-$, which then becomes a condiment in surface and ground waters. Indeed, Cassman et al. (2002) estimated that just 37% of the applied N fertilizer is actually used by maize in the north central U.S. Thus there is a tremendous opportunity to increase N use efficiency in maize production, which should both reduce environmental problems cause by fertilizer N and save farmers a significant amount of money because N fertilizer is the largest single input expense in modem maize production systems. The key to improving N use efficiency in maize production in humid regions is applying the right amount of N fertilizer in the right place at the right time (EPA, 2011).

Soil $NO_3^-$ levels measured in the early spring have long been recognized as a useful tool for predicting N fertilizer needs of crops grown in arid and semiarid regions. However, in humid regions any $NO_3^-$ that is in the soil is vulnerable to leaching and/or denitrification losses during periods of intense rainfall. Thus in humid regions $NO_3^-$ that is present in the soil during the early spring is often lost by the time the growing crop needs it. Later in the growing season, the crop develops an integrated root-mycorrhizal system that is capable of intercepting most soil $NO_3^-$ and preventing leaching losses. However, by then the maize crop may be too tall to allow field access for N fertilizer application and some yield loss due to N deficiency may have already occurred. There exists, fortunately, a narrow window of opportunity in June when the maize is 20 to 25 cm tall during which soil $NO_3^-$ concentrations are predictive of crop response to N fertilizer applications (Magdoff, 1991, Blackmer, 1989). At this critical time the emerging plants have used only a small amount of the available soil $NO_3^-$, yet most of the processes that influence the supply of $NO_3^-$ in soils have already occurred. Furthermore, by this critical time the crop is poised to enter the rapid vegetative growth stage during which high evapotranspiration and high $NO_3^-$ uptake will prevent further leaching and denitrification losses.

The Late Spring Nitrate Test or LSNT (a.k.a., the Pre-Sidedress Nitrate Test or "PSNT") was developed in the 1980s to take advantage of this window of opportunity (Blackmer, 1989; Magdoff, 1990). See those publications, incorporated by reference herein, for details. At the critical growth stage soil samples (integrating 0-30 cm in depth) are collected typically on a 1 hectare grid, brought back to a soil testing lab, and analyzed for $NO_3^-$. If the $NO_3^-$ concentration is above a critical threshold (25 mg/kg), then no additional N fertilizer is applied to the soil. If the $NO_3^-$ concentration is below this threshold, then a sidedress N fertilizer application is recommended (Vagts, 2014). The LSNT and PSNT have been extensively tested and found to have the potential to improve nitrogen fertilizer use efficiency in corn production. See also (Jaynes (2004), incorporated by reference herein, for additional discussion.

Although shown to be effective for improving N use efficiency and reducing leaching losses of $NO_3^-$, the LSNT is not widely used by farmers because labor for soil sampling and analysis are expensive, its low spatial resolution misses substantial in-field variability, and time delays between soil sampling and availability of the prescription N fertilizer map increase risk for farmers. The bottom line for most farmers is that the LSNT is too impractical and too risky for large-scale use on production agriculture fields.

Currently soil nitrate concentrations cannot be measured in-real-time on-the-go in the field, rather it is necessary to physically collect soil samples from agricultural fields, take those samples to a laboratory, and measure soil nitrate level in the samples in a laboratory. Once the samples have been analyzed in the lab, a prescription for nitrogen fertilizer can be written, but typically only at the field scale. Finer spatial resolutions are possible, but generally not practical because of the high cost of collecting and analyzing a large number of soil samples. To be effective in the Midwest corn belt, soil samples must be collected, analyzed and fertilizer applied all during a narrow window of time in the late spring (the late spring nitrate test or LSNT).

Farmers spend more than $1 B per year on nitrogen fertilizer for corn production in Iowa. Fifty to 70% of that nitrogen is lost from the soil (does not end up in the corn plants) through leaching, volatilization and/or denitrification. The leaching of nitrate from agricultural soils is a huge economic loss for farmers and is a major cause of nitrate pollution that is impairing surface and ground water quality in Iowa, in the Mississippi river, and in the Gulf of Mexico.

Veris Technologies, Inc. developed a commercial field mobile near infrared diffuse reflection spectrometry (NIRS) soil sensing system. Veris introduced the idea of using a sapphire window on a steel shank with NIRS. See (Christy (2003) and (U.S. Pat. No. 8,204,689 to Christy, et al.) for details, both incorporated by reference herein. As will be discussed later, in the present invention a Diamond Attenuated Total internal Reflectance (D-ATR) cell replaces the sapphire window used by Veris and an FTIR spectrometer replaces the NIRS spectrometer used by Veris. Also and critical, the present invention is capable of measuring soil nitrate concentrations and hence being used to modulate nitrogen fertilizer applications, while the Veris NIRS system cannot measure soil nitrate concentrations.

In the mid 2000s Linker et al. showed that soil nitrate could be measured using Attenuated Total Internal Reflectance-Fourier Transform Infrared spectroscopy (ATR-FTIR). Linker use a laboratory based instrument and a ZnSe ATR cell. The system use by Linker is not practical for in-field applications because the ZnSe ATR cell would be rapidly destroyed in an agricultural field and lab based FTIR instruments cannot withstand the vibration, temperature extremes, and humidity encountered during field operations.

Therefore Linker et al. demonstrated that ATR-FTIR could be used to measure soil nitrate levels under laboratory conditions only. See (Linker 2004), (Linker 2005), and (Linker 2006) for details, each of which is incorporated by reference herein.

As can be appreciated from the foregoing, there are a number of factors that must be considered when attempting to manage soil nitrogen content. Some are antagonistic to one another. For example, there is variability across a field and adequate spatial resolution of this variability requires soil testing throughout the field. On the other hand, remediation of deficiencies is best indicated by the late spring tests, which give a relatively small temporal window. Soil test accuracy is important to appropriate remediation, but removing soil samples to a remote lab is labor and time intensive. Inadequate spatial resolution and/or inaccurate test results could result in over or under application of nitrogen fertilizer both of which will reduce farmer profits, and over application of nitrogen fertilizer aggravates environmental problems associated with nitrogen fertilizer. These are but a few examples.

SUMMARY OF THE INVENTION

Objects of the Invention

The goal of the project is to develop soil nitrate sensor technology that can be attached to farm implements and used to determine in-real-time on-the-go soil nitrate concentrations with sufficient accuracy (parts per million range) to facilitating precision application of nitrogen fertilizer.

A principal object of the invention is to provide methods, systems, and apparatus which improve over or solve existing problems or deficiencies in the state of the art.

Other objects, features, aspects, or advantages of the invention include methods, systems, or apparatus which can provide one or more of the following:
  a. The system can sense (measure) soil nitrate concentrations in agricultural soils.
  b. The soil nitrate sensing system allows nitrate to be analyzed rapidly in-real-time in the field. By measuring nitrate at multiple locations along with GPS coordinates for each location, the system can be used to rapidly generate a map of soil nitrate concentrations, which can be used as the basis for precision nitrogen fertilizer applications. Alternatively the sensor can be attached to (integrated with) a fertilizer applicator, allowing real time modulation of nitrogen fertilizer application rates based on measured soil nitrate levels. The soil nitrate sensing technology will make the late spring nitrate test (LSNT) practical and cost effective for precision nitrogen fertilizer applications.
  c. We estimate that the soil nitrate sensing system coupled with precision nitrogen fertilizer management has the potential to reduce the amount of nitrogen fertilizer used by corn farmers in Iowa, for one example, by 5 to 20% without adversely impacting corn yields. This reduction in nitrogen fertilizer use could save Iowa corn farmers more than $100 M per year. Estimated improvement in nitrogen use efficiency for corn is 10 to 50%. Similar improvements in nitrogen use efficiency are possible in other grain production systems around the world. Total sales of nitrogen fertilizer in the US are above $8B per year
  d. We have data showing for the first time that the Diamond-Attenuated Total Internal Reflectance-Fourier Transform Infrared spectroscopy (D-ATR-FTIR) nitrate sensor system has enough resolution to be effective for the proposed application. We have a chemometric process to resolve that data (how the data was analyzed and interpreted).

Therefore, objects of the invention can include apparatus, methods, and systems to improve soil nitrogen management in ways which:
  a. are relatively fast (even substantially real-time);
  b. are reliable and reproducible across different fields and soil types;
  c. are cost-effective;
  d. are durable for field use;
  e. can be integrated with remediation systems (e.g. side dress nitrogen fertilizer application).

Aspects of the Invention

In one aspect, the invention comprises a field deployable sensor system that is capable of measuring soil $NO_3^-$ concentrations in the parts per million range. In one embodiment, the sensor system has a sensor tool that is mounted onto the front end of an N fertilizer applicator and the sensor system is used to modulate fertilizer application rates in real-time on-the-go as the applicator moves through an agricultural field. The sensor system will have far greater spatial resolution than is possible with the current 1 ha grid LSNT sampling protocol. Optionally, to integrate $NO_3^-$ measurements over soil depth (0-30 cm depth integration is the current LSNT protocol), we can install more than one sensor, each operating at different soil depths on the same fertilizer applicator or raise and lower the sensor during operation. By continuously raising and lower the sensor during operation in a sinusoidal pattern and synchronize this motion with the integration of the measurements over the time that it takes for the system to complete a full depth cycle (from 15 cm to 30 cm to 0 cm and back to 15 cm depth), we will be able to obtain an average estimate of $NO_3^-$ concentration over the desired depth. This $NO_3^-$ sensor system has the potential to transform the LSNT protocol into a simple and practical tool for precision management of N fertilizer, because it would eliminate the need for soil sampling and the time delay between sampling and fertilizer application.

Another aspect of the invention is to combine the sensor tool with a nitrogen fertilizer application system. The sensor tool would inform the fertilizer application system regarding needed quantity of nitrogen fertilizer. The needed fertilizer could be applied in essentially real-time with the nitrate level sensing (one pass). Alternatively, the fertilizer could be applied at a later time (second pass).

Another aspect of the invention are techniques and methods of obtaining spectra from the soil and processing them. In one example, sensor-to-soil contact is promoted by the ability to adjust pitch of the tool (the base of a steel shank into which a D-ATR cell is embedded) relative the soil. In another example, tool depth is adjustable to allow readings from different soil depths. In another example, specific algorithms for processing the spectra are disclosed.

BRIEF DESCRIPTION OF THE DRAWINGS

Appended to this description are drawings which are identified by Figure number and summarized below.

FIG. 4A is a diagram illustrating pitch adjustment of the tool of FIG. 1.

FIG. 4D is a highly diagrammatic depiction of the ATR arrangement of FIG. 4C, in operative position according to the present invention, for movement across soil in a field and inverted so that the crystal would contact the soil as the tool is moved through the field.

FIG. 7A is a highly diagrammatic depiction of an overall system of on-the-go nitrate sensing and nitrogen fertilizer application according to aspects of the present invention, including enlargements of one sensing tool and one fertilizer injection knife for a liquid fertilizer applicator.

FIG. 10A is a highly diagrammatic view illustrating an Agilent 4100 Exoscan FTIR spectrometer with ATR diamond crystal in the tool of FIG. 1.

FIG. 10B is similar to FIG. 10A but showing a non-limiting alternative example of a D-ATR FTIR combination in the tool of FIG. 1.

DETAILED DESCRIPTION OF EXEMPLARY EMBODIMENTS OF THE INVENTION

Overview

Figure 1:
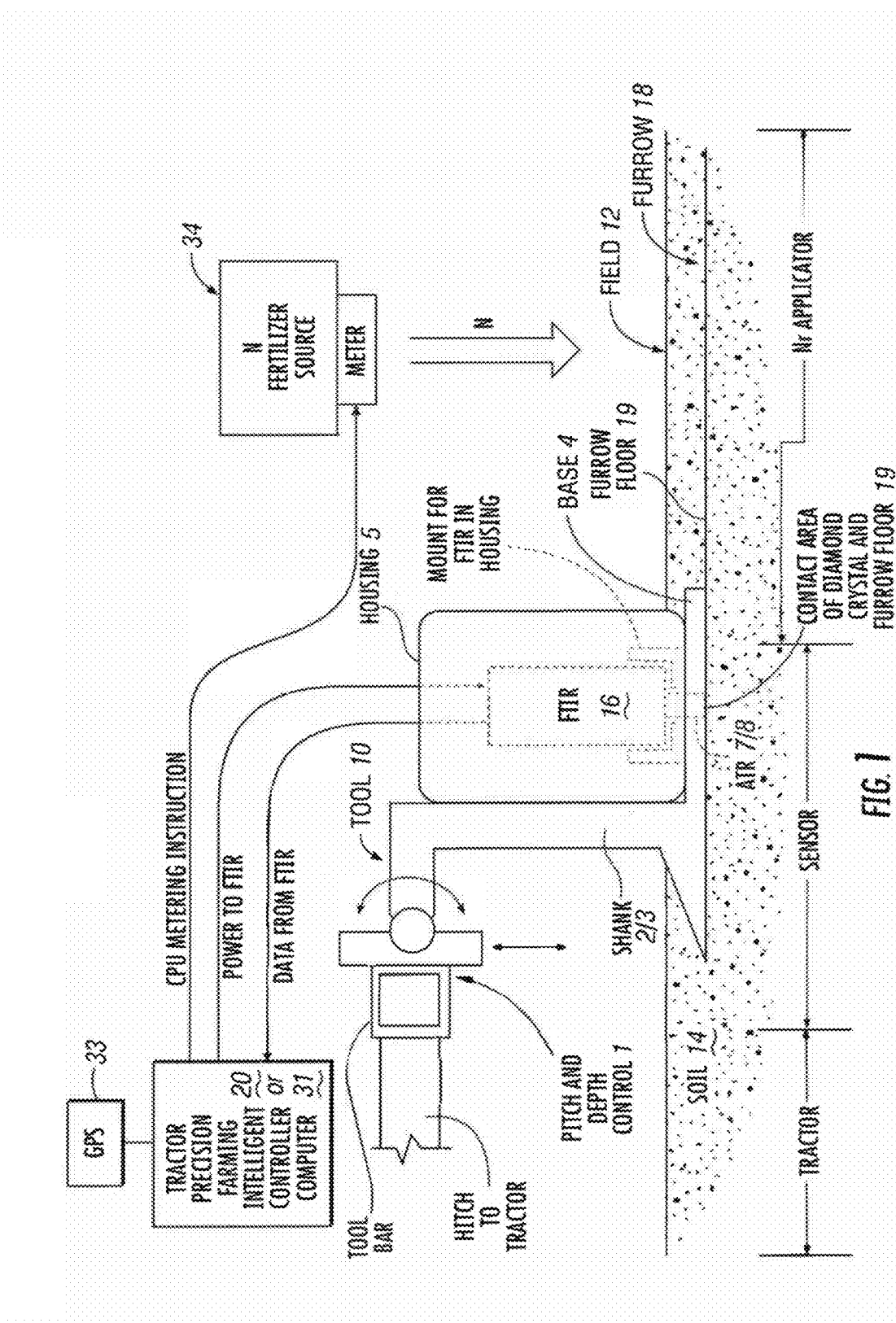
FIG. 1 is a side elevational schematic view of a system according to one exemplary embodiment of the present invention including one example of a nitrate sensing tool and a nitrogen fertilizer applicator.

For a better understanding of the invention and its aspects, several examples of forms it can take will now be described in detail. It is to be understood that these exemplary embodiments are for illustrative example only, and are neither inclusive nor exclusive of all the forms the invention can take. Variations obvious to those skilled in the art will be included within the invention, which is not limited to the specific embodiments below.

Reference will be made from time to time to the Drawings (summarized above). Reference numbers will be used to indicate certain parts or locations in the drawings. The same reference numbers will be used for the same or similar parts or locations throughout the drawings unless otherwise indicated.

Approach: We use Fourier Transform Infrared (FTIR) spectroscopy as the basis for the soil $NO_3^-$ sensor system. Until recently several factors have precluded the use of FTIR as a sensor to determine soil $NO_3^-$ concentrations: (1) FTIR instruments are too expensive for this application, (2) FTIR instruments are delicate laboratory instruments that cannot tolerate dust, vibration, moisture and shock that are encountered during an agricultural field operation, and (3) traditional transmission FTIR sample presentation techniques require significant sample preparation and are not compatible with a field mobile on-the-go system. In recent years these limitations have diminished with the development of relatively inexpensive, portably and ruggedized FTIR systems designed for military, homeland security, law enforcement and other applications (examples include Thermo Scientific TruDefender FT and Agilent 4100 Exoscan FTIR Spectrometer, commercially available from Thermo Fisher Scientific168 Third Ave., Waltham, Mass. (USA) and Agilent Technologies, 5301 Stevens Creek Blvd., Santa Clara, Calif. 95051 (USA)), respectively. Furthermore, development of Transient Infrared Spectroscopy (TIRS), Diffuse Reflectance (DRIFTS), and Attenuated Total Internal Reflectance (ATR) sampling presentation systems provide the option of directly observing neat soil, and hence are potentially compatible with field mobile on-the-go $NO_3^-$ sensing.

Of the various options, ATR-FTIR with a diamond ATR cell can be the most suitable sample presentation system for the proposed application, because the optical surface of the diamond is in direct contact with the soil and because the spectrometer can be fully protected from the elements inside of an enclosure (e.g. hardened steel) and hence the optical path is protected from debris, dust and moisture. The only component that would be exposed would be the optical surface of the diamond in the ATR cell, which would be in direct contact with moving soil and would be continuously refreshed by the moving soil. The rest of the ATR cell can be made of robust materials such as hardened steel (except the diamond) and embedded in a similarly robust (e.g. hardened steel) plate on the bottom of a steel or other robust material shank. Diamond is the hardest material known to science and therefore will be robust and not damaged by soil abrasion as the system is moved through the soil. A sapphire window, such as used in the Veris NIRS system will not work for this application because sapphire is not transparent to mid-infrared radiation. ATR cells made of other materials, such as the ZnSe ATR cell used by Linker et al., 2004 and 2005, are soft and would be rapidly destroyed by soil abrasion in this application. The open optical path required for TIRS-FTIR and DRIFTS-FTIR systems as proposed by Jones et al., 2013 (incorporated by reference herein) would have to be protected from dust and moisture while operating in the field, and thus these systems would be more vulnerable to damage and operation failures than a Diamond-ATR-FTIR system.

Potential Impact: The disclosed sensor system has the potential to substantially improve N use efficiency in maize production thereby saving farmers money and reducing the offsite environmental impacts of N fertilizer use in agriculture. At the watershed scale, adoption of the LSNT N fertilizer management system has been shown to reduce $NO_3^-$ concentrations in stream water by >30% relative to fall N fertilizer applications (Jaynes 2004). The reduction in $NO_3^-$ leaching was achieved without loss of grain yield thus implying a ~30% increase in N use efficiency. Similarly, Bausch and Diker (2001) (incorporated by reference herein) reported that in-season variable rate N fertilizer applications based on crop canopy sensing reduced the amount of N fertilizer needed to obtain comparable maize yields by 39.2 kg ha$^{-1}$. Use of the disclosed soil $NO_3^-$ sensor system for precision modulation of N fertilizer application rates is anticipated to perform as well or better than LSNT and crop canopy sensing to reduce nitrate leaching and improve N use efficiency in maize production. A key difference is that the soil $NO_3^-$ sensor system is anticipated to be widely adopted by farmers because it does not require additional labor for soil sampling or risky time delays, which are associated with the LSNT and crop canopy sensing systems.

Deployment of the envisioned $NO_3^-$ sensor based precision N management system across the 92M acres of maize grown in the U.S. would go a long way towards meeting the EPA goal of reducing $NO_3^-$ loads in the Mississippi river by 45% that was articulated in the 2008 Gulf Hypoxia Action Plan and the Mar. 16, 2011 memorandum entitled, "Recommended Elements of a State Framework for Managing Nitrogen and Phosphorus Pollution" (Stoner 2011) (incorporated by reference herein). Furthermore, by improving N use efficiency the system has the potential to significantly reduce the amount and hence cost of N fertilizer needed for crop production.

Generalized Embodiments

One aspect of the present invention is using a Diamond-Attenuated Total Internal Reflectance-Fourier Transform Infrared Spectrometer (D-ATR-FTIR) system as afield-mobile soil nitrate sensor, and to use the D-ATR-FTIR sensor system to measure soil nitrate levels in the late spring, and to use data generated by the D-ATR-FTIR soil nitrate sensor to spatially modulate nitrogen fertilizer applications to agricultural fields based on protocols described in the Late Spring Nitrate Test (LSNT). Another aspect is the idea to physically raise and lower the soil nitrate sensor system (modulate the depth of the sensor in the soil) while the system is in motion and being used so as to obtain an average soil nitrate reading for the rooting zone, which is required in the LSNT protocol.

Specific Apparatus (Sensing Tool)

With reference to FIGS. 1-3 and 11, an exemplary embodiment of a tool 10 for sensing soil nitrate levels will now be described.

Figure 11:
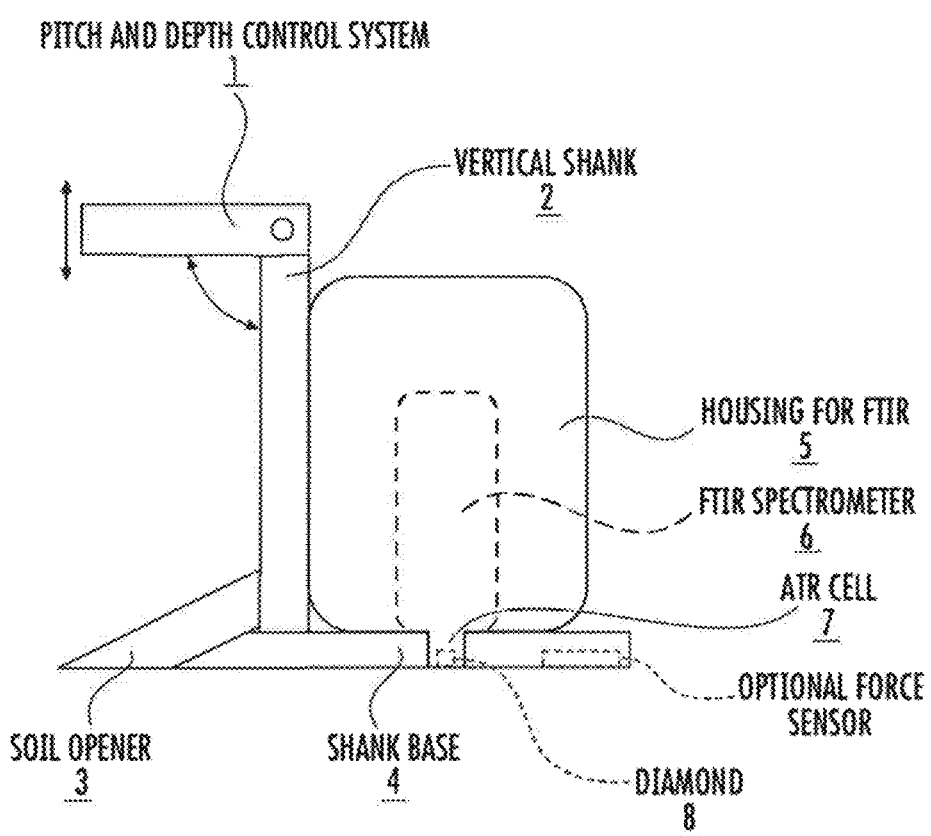
FIG. 11 is a side elevation schematic of the sensing tool of FIG. 1 in isolation.

The sensor 10 includes a housing 5 containing a ruggedized Fourier Transform Infrared spectrometer 6 (FTIR) equipped with a Diamond-Attenuated Total Internal Reflectance cell 7 (D-ATR-FTIR), all riding on a steel shank system 2/3/4 designed to interface the D-ATR-FTIR with the soil 14 in a field 12. The spectrometer 6 would be operatively connected (e.g. via hard-wiring) to a computer 20 (e.g. located in a tractor cab) and algorithms used to interpret the signal coming from the D-ATR-FTIR. FIGS. 1 and 11 are schematic diagrams showing the basic components of the tool 10:

1) The pitch and depth control system 1 is a mechanical mechanism designed to control the depth to which the shank base 4 penetrates into the soil 14 and the pitch of the shank base 4 relative to the soil surface 16. Tool 10 is attached to a tractor or other vehicle which pulls the sensor shank system 2/3/4 through an agricultural field 12.
2) The vertical shank 2 provides the primary structural support for tool 10.
3) The soil opener 3 is a steel plow sheer or blade designed to open a furrow 18 in the soil 14.
4) The shank base 4 is a flat piece of steel designed to slide smoothly along the bottom 19 of the open soil furrow 18.
5) The FTIR housing 5 is a containment vessel designed to support and protect the FTIR spectrometer 6 and other contents during field operations.
6) The FTIR spectrometer 6 is a ruggedized instrument capable of operating under harsh conditions (withstand shock, vibration, and extremes of moisture and temperature).
7 & 8) The diamond ATR cell 7/8 is the interface between the FTIR spectrometer 6 with the soil surface 19. A hole 9 in the shank base 4 allows the diamond 8 ATR cell 7 to be inserted through the shank base 4 such that the diamond 8 of the ATR cell is in direct contact with the soil surface at the bottom 19 of the opened furrow 18.

An option would be to add a wear plate around the exposed surface of the diamond. One example would be sapphire, machined basically in a donut shape, surrounding the diamond surface and then protecting the ATR cell from abrasion. Sapphire has reasonable durability properties for this use. Other materials are possible.

One example of FTIR 6 is an Agilent 4100 Exoscan FTIR Spectrometer (commercially available from Agilent Technologies, Inc., of Santa Clara, Calif., USA). See FIG. 10A and spec sheets available at www.amgilent.com/cs/library/brochures/5990-8097EN_4100-Exoscan-FTIR-Brochur.pdf, incorporated by reference herein, which discuss operating ranges and characteristics, as well as diamond ATR cell, and FTIR; as well as software choices and different formats of data output.

In recent years, robust FTIR systems have been developed for military and homeland security applications (examples include Thermo Scientific TruDefender FT and Agilent 4100 Exoscan FTIR Spectrometer). These new FTIR instruments have been ruggedized so that they can be use on a battle field or in other harsh environments. Furthermore, these new ruggedized FTIR instruments have been equipped with diamond ATR cells. Diamond ATR cells are hard enough to survive field conditions. FIG. 10B diagrammatically illustrates the Thermo Scientific TruDefender FT mounted inside housing 5. See tools.thermofisher.com/content/sfs/brochures/TruDefender-FT-SpecSheet.pdf, incorporated by reference herein, for information about it.

Mid-infrared spectroscopy (mid-IR spectroscopy) is a well-known type of spectroscopy, which can be used with various sample presentation modes (e.g., transmission, diffuse reflectance, photo-acoustic, transient infrared, and attenuated total internal reflectance) to produce an infrared spectrum (essentially a graph of infrared light absorbance on the vertical axis vs. frequency or wavelength or wavenumber on the horizontal axis; typically the wavenumber scale is used with units of $cm^{-1}$). A common laboratory instrument that uses this technique is a Fourier transform infrared (FTIR) spectrometer.

Attenuated total reflection (ATR) is a sampling technique that can be used with mid-IR spectroscopy to enable samples to be examined directly in the solid or liquid state without further preparation. ATR is typically an attachment to an infrared spectrometer that directs light toward a crystal of high refractive index that is transparent to the infrared radiation (light). The optical surface is one of the crystal facets that can be placed in direct contact with a sample. Any light that impinges on the optical surface from within the crystal at an angle less than the "critical angle" will be totally reflected back into the crystal as long as the material in contact with the optical interface (the sample) has a lower refractive index.

The reason contact between the ATR crystal and the sample is important is because ATR relies on an evanescent wave (a property of total internal reflection or TIR) that is propagated across the optical surface of the ATR crystal and only penetrates 0.5 and 2 micrometers into the sample and hence interrogates only a very thin slice of the sample that is in direct contact with the optical surface of the ATR crystal. The exact penetration depth of the evanescent wave into the sample depends on the wavelength of light, the angle of incidence and the indices of refraction for the ATR crystal and the medium being probed.

As an evanescent wave interacts with a sample in direct contact with an ATR crystal, the intensity of the infrared radiation is selectively attenuated at different frequencies depending on the chemistry of the sample which is in direct contact with the optical surface. This process of selective attenuation is what actually generates the ATR-FTIR spectra. The presence of air bubbles or gaps at the interface of the sample and the optical surface degrades the spectra, because the evanescent wave is probing air not sample. Therefore, the quality of ATR-FTIR spectra are improved with a more direct and intimate contact between the sample and crystal surface. In one aspect of the invention, forward motion of the nitrate sensor system through the soil and a slight positive tilt on the base of the steel shank promotes this crystal/soil contact by ensuring that soil is continuously being pressed against the optical surface of the diamond ATR cell. This constant pressure express water from the soil onto the optical surface of the ATR cell, which enhance the $NO_3^-$ signal because $NO_3^-$ is primarily in the aqueous (soil water) phase. Therefore the design inherently enhances the D-ATR-FTIR $NO_3^-$ signal due to the forward motion of the sensor through the soil and the positive tilt on the base of the steel shank.

Figure 4B:
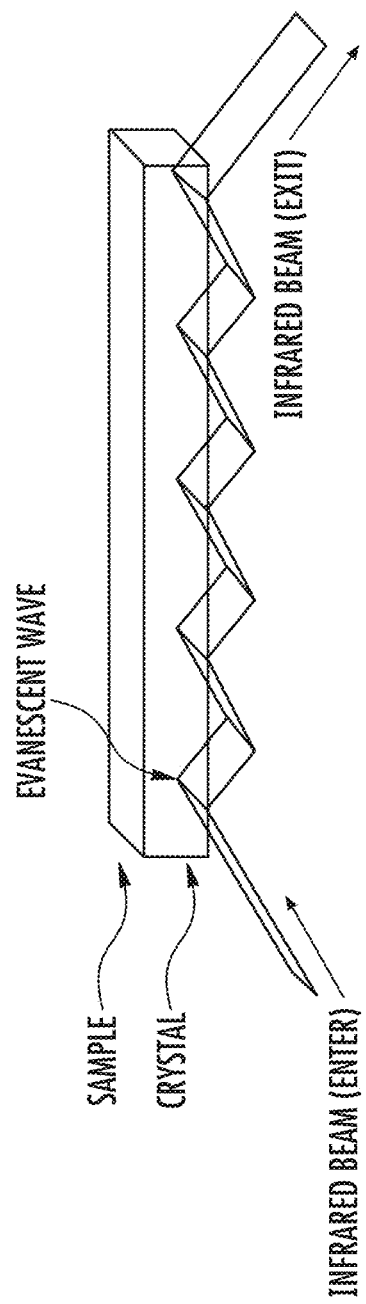
FIG. 4B is a highly diagrammatic depiction of how attenuated total internal reflectance (ATR) technique interrogates a sample with an evanescent standing wave generated by total internal reflection (TIR) in an ATR crystal and which extends a small distance outside the crystal into a sample under investigation; here illustrating a multiple reflection technique.
Figure 4C:
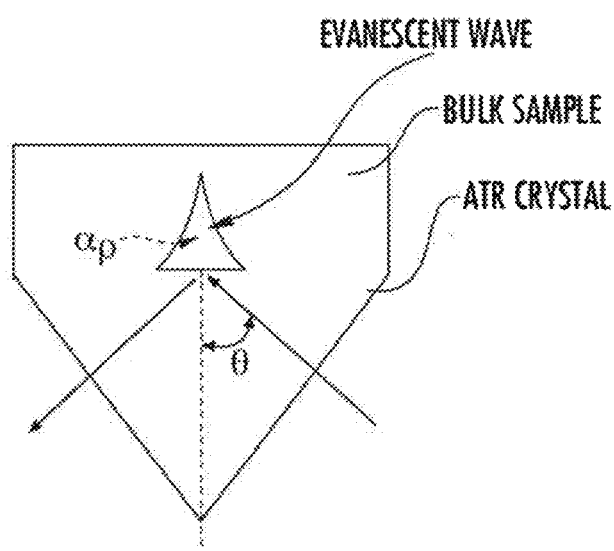
FIG. 4C is a highly diagrammatic depiction of how ATR interrogates a sample with an evanescence standing wave generated by total internal reflection (TIR) in an ATR crystal and which extends a small distance outside the crystal into a sample under investigation; here illustrating a single reflection technique.

See shop.perkinelmer.com/content/TechnicalInfo/TCH_FTIRATR.pdf; en.wikipedia.org/wiki/Attenuated_total_reflectance www.azom.com/article.aspx?ArticleID-5958; chemwiki.ucdavis.edu/Analytical_Chemistry/Instrumental_Analysis/Spectrometer/ATR-FTIR (now chem.libretexts.org/Core/Analytical_Chemistry/Instrumental_Analysis/Spectrometer/ATR-FTIR); www.specac.com/products/golden-gate-atr-ftir-accesory/standard-golden-gate-diamond-atr-accessory/513, each incorporated by reference herein FIGS. 4B-D for additional information regarding ATR and FTIR. The basic principles of ATR are illustrated and described in FIGS. 4B-C and the references cited above, including the difference between multiple reflection ATR (FIG. 10A) and single reflection ATR (FIG. 10B). The cited references discuss the reliability and sample-to-sample reproducibility of ATR FT-IR spectroscopy, as well as factors in utilizing single reflection versus multiple reflection techniques. It also allows fast spectral acquisition. Diamond as the internal reflection element or crystal is durable, can take high forces, and can be small (e.g. on the order of 2 mm diameter) for good sample-to-crystal contact and improved spectral acquisition. In the present described embodiments, single reflection technique has been found to be a good candidate for a number of reasons.

As illustrated diagrammatically in FIG. 1, tool 10 can be incorporated into an overall system that could include a tractor 30 (or other motive force), which would pull a toolbar 32 (or other frame) through the field 12. Tool 10 would be attached or mounted by any number of techniques to toolbar 32. Tool 10 not only can penetrate the surface 16 of the field soil 14, but promote good contact between the optical surface of the diamond 8 of the ATR cell 7 and the soil 12 as tool 10 is pulled through field 12, and carry the components needed to obtain the spectral information to process into a nitrate level prediction. One feature of this embodiment is the basic nature of the tool. Only the components needed to obtain good soil-to-ATR contact and spectral acquisition are in the tool. Processing of the spectral information can be elsewhere. One example is to have the computer and software to do so in the substantially protected environment inside a tractor cab. It may even be possible to utilize existing digital controllers or processors, such as with in-cab precision farming systems. Appropriate communication protocol between spectrometer and computer would need to be set up. Splitting the components of the system of this embodiment of the invention in that manner can assist in economy, durability, and reduced size and weight at the tool. As will be appreciated by those skilled in the art, the tool can be used with late spring nitrate test (or similar). This would involve moving the tool through the soil after the plants have emerged. Therefore, compactness can be important when penetrating the soil between row crops. The overall system using tool 10 will be described in more detail later. But as indicated in FIG. 1, in one embodiment, a fertilizer applicator 34 could also be pulled along with tool 10 and nitrate predictions from tool 10 could be communicated to a controller which would use those predictions to modulate the amount of nitrogen fertilizer applied.

Figure 7B:
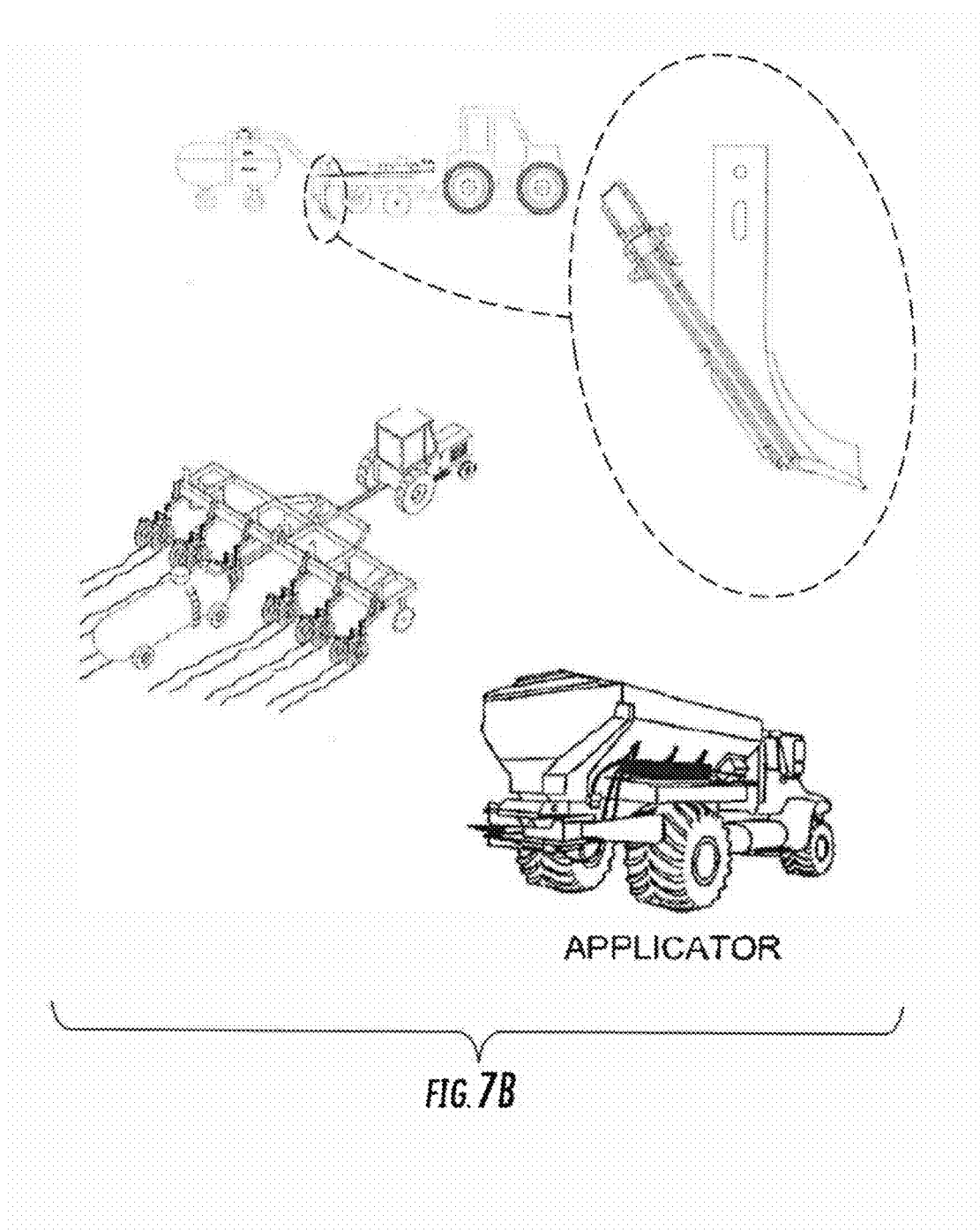
FIG. 7B are illustrations of three non-limiting examples of fertilizer applicators of the types that could be used with the present invention.

In the example of FIG. 1, fertilizer applicator could be a conventional anhydrous ammonia tank 35 (shown schematically; see also FIG. 7A). Injection knives 36, each with a tube 37 in fluid communication to valving 38, are used to inject the composition into the soil. Valving 38 could be controlled to modulate the quantity injected. The system could also be used to modulate fertilizer applicators spreading dry fertilizer (such as urea, $KNO_3$, etc.) or liquid fertilizers (such as urea ammonium nitrate "UAN" in 28 or 32% solutions). Such is well-known in the art. See FIG. 7B.

In the example of FIG. 1, tool 10 can include both electrical power and data connections from and to a computer 20 (or other programmable processor). Many tractors/motive forces have on-board an intelligent controller (indicated diagrammatically at reference number 31), which is used in precision farming. Intelligent controller 31 can include processing capability, have various memory storage, and inputs and outputs to receive data from a variety of sources and sensors and then instruct operations of both tractor and implements related to the tractor. One of the inputs could be a GPS unit (also on-board the tractor cab). In this case, tool 10 could communicate (e.g. on a continuous or substantially continuous basis) acquired spectral readings from the spectrometer for generation of both nitrate level predictions and correlated georeference for each of those predictions by the cab-mounted computer or intelligent controller. Field maps could be generated of the correlations. Intelligent controller 31 could use that map to instruct modulation of nitrogen application from applicator 34. This would allow fertilizer application at a later time and in a second pass through field 12. But alternatively, as mentioned previously, computer 20 or intelligent controller 31 could receive nitrate level predictions in essentially real-time and modulate fertilizer application rates immediately. This might not need any geo-referencing, although the data from such on-the-go real-time applications could be saved along with geo-referencing as a record of fertilizer application to facilitate other management decisions and/or research.

Figure 2:
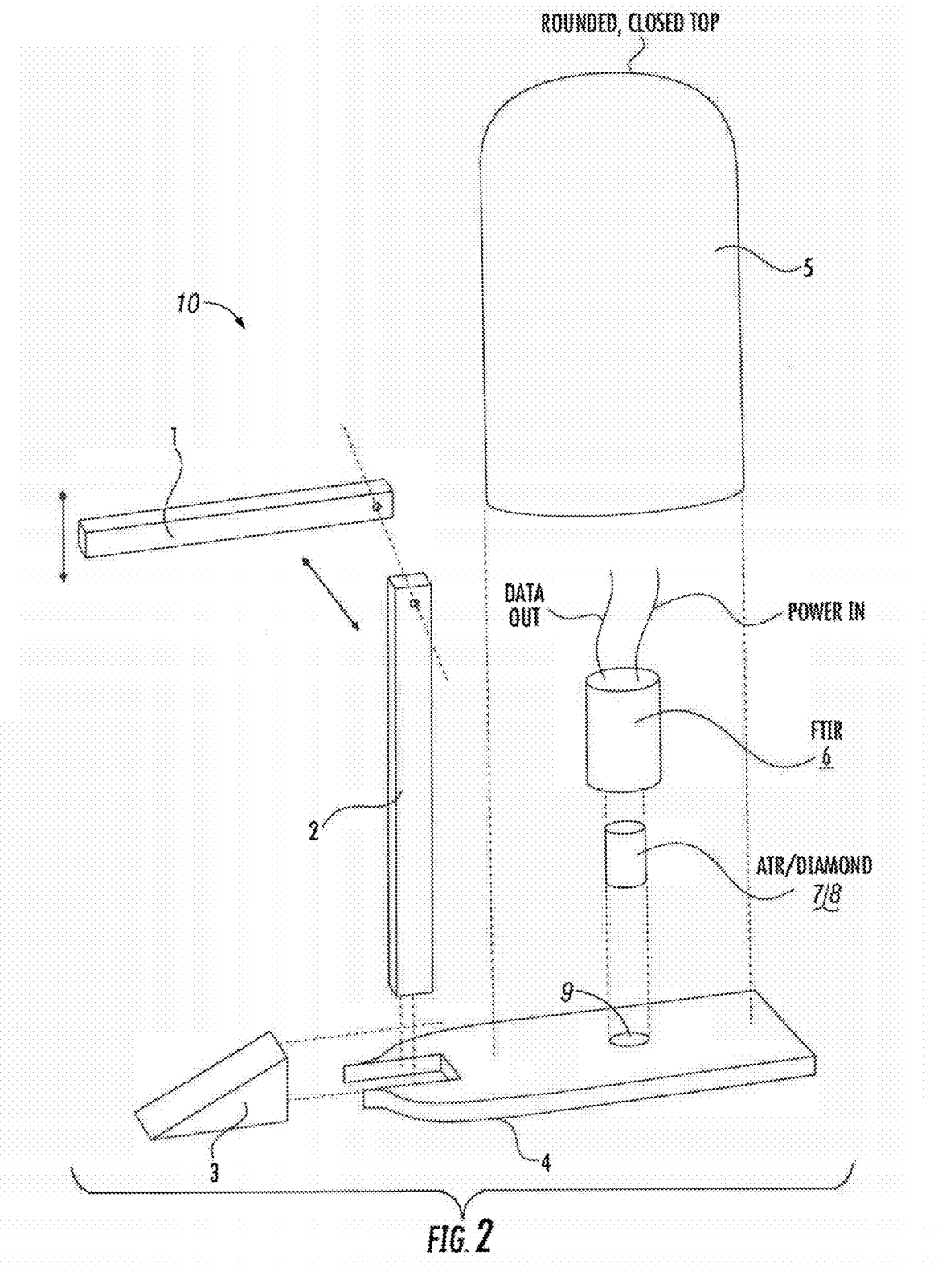
FIG. 2 is a perspective exploded view of the nitrate sensing tool of FIG. 1.
Figure 3:
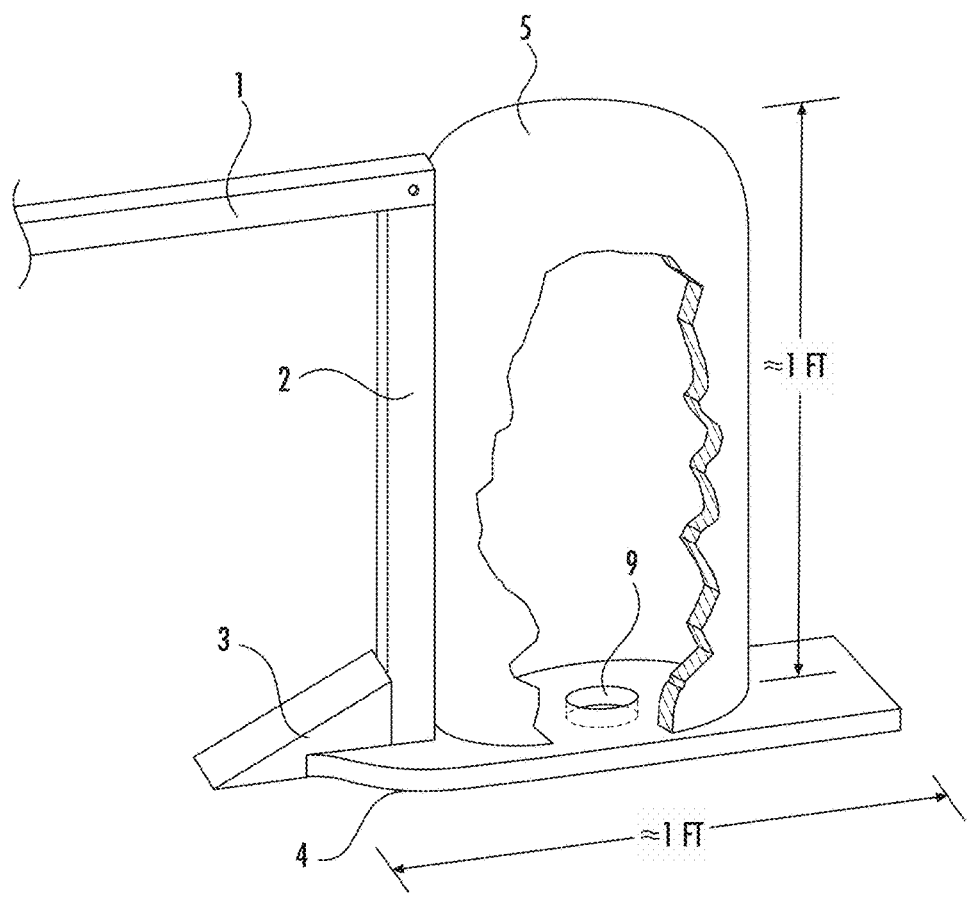
FIG. 3 is an assembled view of the tool of FIG. 1, with a portion of the housing cut-away and without other system components, such as a D-ATR cell or spectrometer.

FIGS. 2 and 3 illustrate the basic components of tool 10 and how they would be assembled. Base 4 can be essentially a flat (e.g. metal) piece with through-hole 9. As indicated at FIG. 1, when dragged along the ground, this would promote diamond optical surface 8, which is essentially flush with the bottom side of base 4, to be in abutment with soil 14. This promotes collection of high quality spectra by the FTIR spectrometer 6. Through-hole 9 would be formed to be closely complementary with diamond 8 and/or would be sealed when assembled. The flat bottom of base 4 would help tool 10 move smoothly along bottom 19 of furrow 18, here formed by soil opener 3 (e.g. metal) which is attached (e.g. welded) to the front of base 4. As illustrated, soil opener 3 can essentially be a soil cutting or penetrating tool. It could take a number of configurations. Vertical shank 2, e.g. metal, could also be welded to base 4. The combination 2/3/4 would thus form an integrated and rigid subassembly.

In this example, subassembly 2/3/4 is attached to arm 1 (e.g. metal), which can be operatively connected to tractor 20 (e.g. by attachment to a tool bar 32, which is hitched to tractor 20). As schematically indicated, subassembly 2/3/4 can be adjusted relative to arm 1, and thus relative to soil 14. In this example the adjustments are both pitch and depth.

As can be appreciated by those skilled in this technical field, the manner in which such adjustments can be effected can vary. For example, hydraulic, mechanical, or electro-mechanical actuators (or combinations of the same) could pivot vertical shank 2 relative to arm 1 around a pivot to change pitch of base 4. Likewise, hydraulic, mechanical, or electromechanical actuators (or combinations of the same) could move arm 1 up and down to change depth of base 4. By calibration techniques within the skill of those skilled in the art, an operator could instruct such actuators with controls in the tractor to make such adjustments on-the-go.

Examples of actuators that could be used to adjust parts on an agricultural implement are shown in U.S. Pat. No. 8,204,689 to inventors Christy, et al., incorporated by reference herein, which also illustrates ground-working components that can open the soil and make a furrow.

An example of a shank 2/3 is Model 6/DT Subsoil Ripper (part #125-027-01) commercially available from Orthman Manufacturing, Inc. of Lexington, Nebr. (USA). Portion 3 can be the soil-soil ripper and portion 2 the shank up to a support and actuator to adjust pitch and depth. Others are possible.

As will be appreciated by those skilled in the art, with reference to the Figures and this present description, one form the tool 10 can take is basically on the order of one to several feet long and a foot or less in width, with vertical shank 2 of a sufficient length, width, and thickness to extend to the pitch and depth adjustment. The thickness and materials for these parts can be steel of on the order of the range of ½ to an inch thick. As such, it can be robust enough to penetrate and move through all types and conditions of typical crop soil, but also be small enough to travel between crop rows without disrupting or destroying plants. As discussed elsewhere, one beneficial use of tool 10 can be in association with late spring nitrate testing (LSNT) or similar, when field crops have emerged. Pitch adjustment can also be managed to control the amount of drag (how much force needed to pull the tool through the soil) in balance with obtaining soil-to-diamond contact. Also depth can be controlled to better obtain readings throughout the top 30 cm or so of soil to match up with some of the late spring tests such as LSNT or similar. For example, the computer or other controller of depth adjustment could continuously adjust depth between approximately 0 cm below average soil level and 30 cm below that level (basically in a sinusoidal path relative a vertical plane through the field). An average of the signal collected through each full depth cycle could be computed by the computer to get an average nitrate for the upper 30 cm of soil.

Housing 5 can be a hardened metal casing with interior space to enclose ATR 7, FTIR 6, and other components. In this embodiment, because computer 20 and a GPS unit 33 are on the tractor, the size of housing 5 can be minimized to just encase the spectral acquiring components which, again, minimizes overall size and weight. Housing 5 would be welded to base 4 or shank 2 and have a door or panel that could be sealed in operation but opened if needed for such things as maintenance or repair of internal components. Alternatively, housing 5 could be removably fixed to tool 10 by fasteners such as screws, bolts, clamps, keys and slots, or other techniques. Internal components could be mounted to base 4 or the interior of housing 5 with shock and vibration absorbing or cushioning interfaces (e.g. polyurethane foam). Padding or cushioning could be imposed between components. Electrical connections (wires and connectors) between components and then external from housing 5 could be ruggedized. Any openings could be sealed.

The particular way the spectrometer and ATR cell are mounted inside housing 5 and relative to base 4 can vary. FIG. 1 indicates diagrammatically that there can be some sort of mount, receiver, or bracket to do so. FIGS. 10A and B diagrammatically depict two different commercially available D-ATR-FTIR combinations that might be used inside housing 5. A bracket or mounting would need to be added and be able to hold the D-ATR-FTIR combination in operative position as tool 10 is dragged through a field. One advantage of at least some of these commercially-available D-ATR-FTIR units is that they do not need any moving parts. Therefore, a fairly rigid and secure mounting to base 4 is possible, particularly to promote as good and consistent of contact of the optical surface of diamond-ATR to the soil as tool moves through it. This, as well as typical movement of tractor, tool bar, and shank combination 1-4 through somewhat uneven, sometimes cloddy or rocky soil, can cause some bouncing of base 4 relative to the soil. But by having substantially continuous operation of the spectrometer, promotion of diamond-to-soil contact, and/or other features of this embodiment, sufficient quality of spectral acquisition is encouraged.

As can be appreciated, tool 10 is relatively compact, has a relatively few parts, and is robust for field conditions, yet can be adjusted positionally for beneficial purposes. FIGS. 4A-D and 5A-B illustrate two of those adjustments.

As shown in FIG. 4A, tool 10 penetrates surface 16 of soil 14. That surface is rarely smooth. It can include soil clods, rocks, or debris. It can be quite hard or compacted, or it can be relatively moist, or somewhere in between. A furrow 18 is created by leading edge soil opener 3. Base 4 is essentially a tail behind opener 3. If base 4 is held essentially parallel with the bottom 19 of furrow 18 (as shown in solid lines in FIG. 4A), the bottom of base 4 would move along the same depth as the bottom of soil opener 3. This may work adequately to keep diamond 8 in substantial contact with soil 14. However, it has been discovered that better results can be possible by adjusting the pitch of tool 10 in the direction illustrated in dashed lines in FIG. 4A (which is exaggerated to show the general principle). By changing pitch by an angle a, soil opener 3 pivots slightly up and tail 4 pivots slightly down. Leading edge 3 therefore cuts a shallower initial furrow. However, the bottom of trailing tail 4 must essentially make a deeper furrow instead of following the initial depth of cut of leading edge 3 (compare furrow bottom 19 in bold lines to furrow bottom 19 in dashed lines). The bottom of base 4 is essentially more exposed to and must push on soil 14, including at the location of diamond 3. This promotes better direct contact between soil 14 and diamond 3.

In this embodiment, the amount of pitch adjustment (angle a) can be in the approximate range of 0 to 20 degrees: and perhaps more often than not 0 to 10 degrees. A balance is made between amount of angle versus increased resistance and wear and tear. The angle can be set and left for an entire field. It can be adjusted from time to time. It might even be adjusted on the fly. For example, a sensor (not shown), such as a force sensor (e.g. model M16 Heavy Industrial Pressure Transducer from vendor TE Connectivity) could be attached to the tractors hydraulic line for hydraulically controlled systems, alternatively direct pressure sensors might be mounted on the bottom of base 4, or at the actuator that adjusts pitch, and pitch constantly adjusted (including perhaps automatically) based on a predetermined required amount of force that has been determined to promote good diamond-to-soil contact. As can be appreciated, at a minimum, this backward pitch can promote better diamond-to-soil contact as the tool 10 is pulled through a field and the soil, the tractor, or the tool experiences bumps, vibrations, and the like. See schematic optional placement of such a sensor in FIG. 11.

FIGS. 4B-4D illustrate additional principles about use of a D-ATR and the variable pitch adjustment. FIGS. 4B and C illustrate diagrammatically the operational principles of ATR. See also the above-cited references for factors regarding multiple reflection ATR (FIG. 4B) or single reflection ATR (FIG. 4C). Total internal reflection (TIR) in the diamond, and appropriate other conditions for ATR, produce the evanescent standing wave that extends outside the diamond. FIGS. 4A and B show the ATR cell inverted from its position in tool 10. The standing wave $\alpha\rho$ extends outside the diamond and interacts with the sample (e.g. soil) according to known physics principles. In certain regions of the spectrum where the sample absorbs energy from the standing wave, the standing wave is attenuated. This attenuated energy is passed back into the IR beam in the diamond. Spectra generated from this IR beam can be processed to relate the attenuation to chemical composition of the soil, including nitrate level.

FIG. 4D diagrammatically shows the single reflection technique of FIG. 4C applied to tool 10. A slight backward pitch adjustment to shank 4 basically tilts the small (e.g. 2 mm diameter) exposed portion of the diamond to the direction of travel of tool 10. This tends to press the diamond more against the soil than if more parallel to the trough/furrow (which would more involve the diamond sliding across the top of the trough). While the negative pitch is not necessarily required for operation, it can promote better spectral acquisition.

Figure 5A:
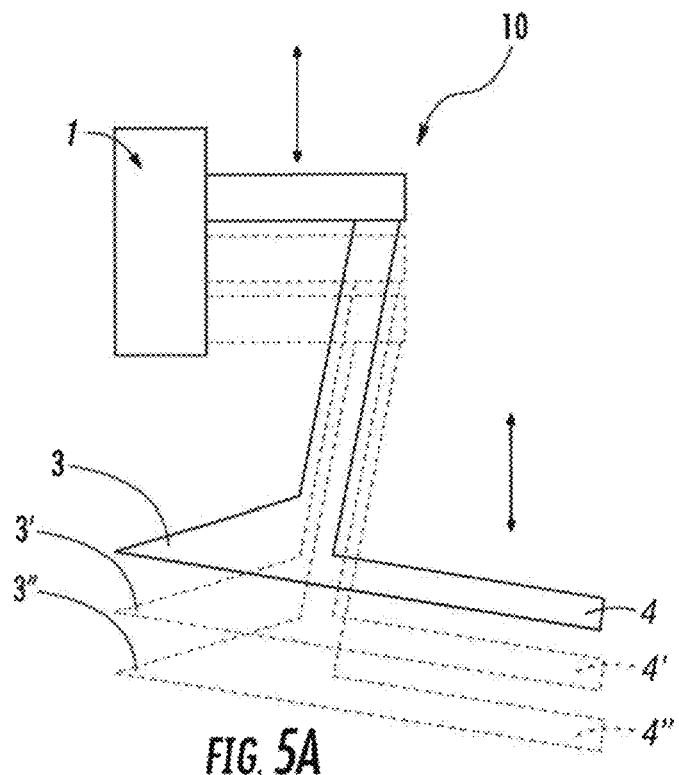
FIGS. 5A and B are diagrams (side elevation and front elevation respectively) illustrating depth adjustment of a single tool of FIG. 1.
Figure 5B:
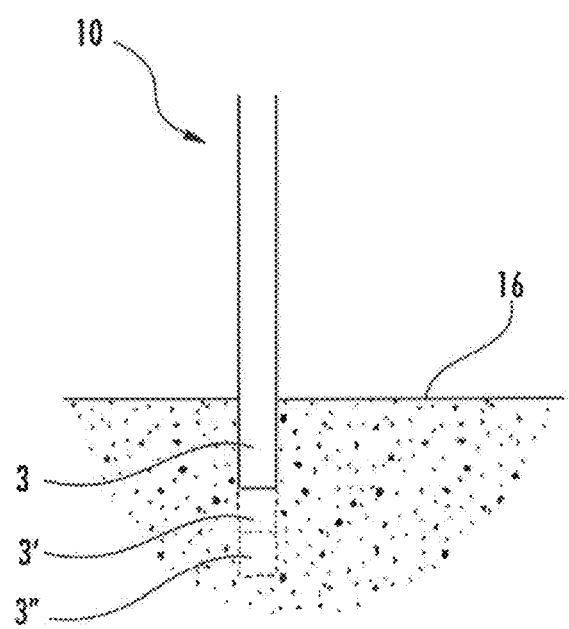

FIGS. 5A and B illustrate diagrammatically one form of depth adjustment of tool 10. As will be explained more below, it can be beneficial to obtain spectra at different soil depths in a field. Allowing the whole tool 10 to be raised and lowered, including on-the-fly, can facilitate this. The range of adjustment can be in the approximate range of 0-40 cm, and perhaps 0-30 cm, but a larger or smaller range is, of course, possible. In one example, tool 10 can start out at a first depth (soil opener 3 in solid lines). By adjustment, a lower second depth (soil opener is dashed lines at position 3') can be quickly made and readings taken at that lower depth. Similarly, a still lower third depth (position 3" of the soil opener) is possible. This depth adjustment could be controlled automatically from computer 20 or intelligent controller 31 to an actuator at tool 10. The actuator could be calibrated to move between, for example, 0 cm relative to average depth of the bottom of shank 4 relative the soil (ref. no. 4), 15 cm lower (ref. no. 4'), and 30 cm lower (ref. no. 4"). The results from each depth could be averaged relative to use with, for example, the LSNT or similar. Other ways to sense or feedback depth are possible.

Figure 6A:
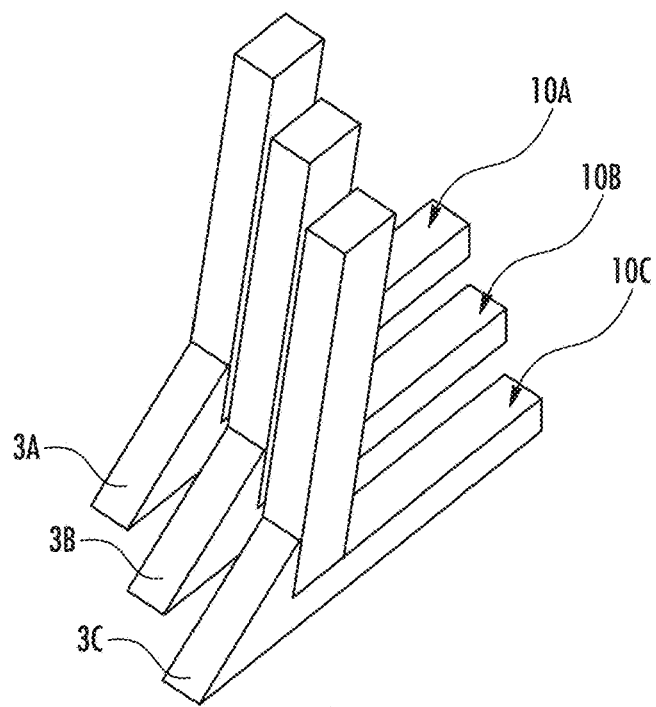
FIGS. 6A and B are diagrams (perspective and front elevation respectively) of an alternative way to sense at different soil depths, wherein three separate tools 10A, 10B, and 10C are pulled together through the soil, each at a slightly different depth.
Figure 6B:
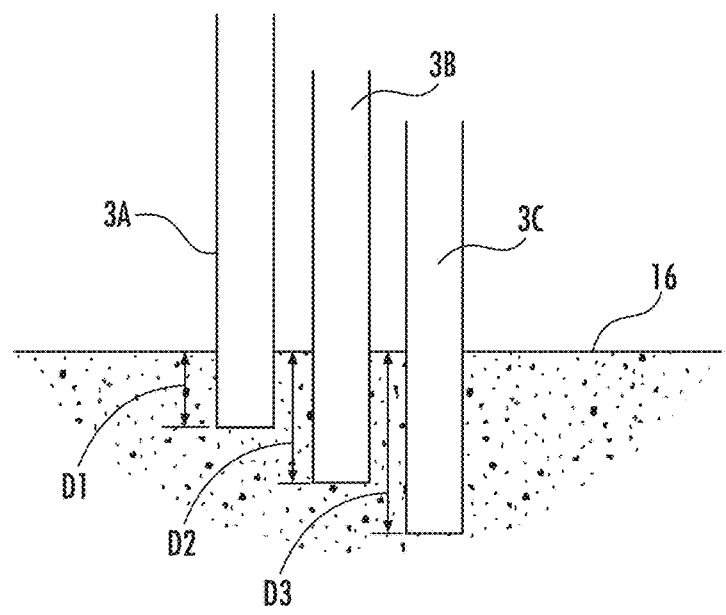

FIGS. 6A and B illustrate an alternative way to get readings from different depths. Instead of moving a single tool 10 up and down in the field, the tool can comprise three separate tools 10A, 10B, and 10C moved through the field at the same time, but each at a different depth (tool 10A and its opener 3A at shallowest depth D1; tool 10B and its opener 3B at a middle depth D2; and tool 10C and its opener 3C at deepest depth D3). By appropriate operation, readings can be collected continuously and simultaneously from all three tools 10A-C. The system would then have those readings for wherever the tractor goes in the field. Alternatively, the system might simply switch between tools 10A, 10B, and 10C and sequentially collect readings so that different depths are probed at different times. As can be appreciated, tools 10A-C could be placed near one another, or they could be separated (e.g. on a single tool bar or on separate tool bars). Also, if plural tools 10 are mounted on the same implement, each could be independently adjustable for either depth or pitch, or both. It may be that each tool 10A-C would be in series rather than in parallel, so as to take up less side-to-side space when moved through a late spring field with emerged plants. Still further, multiple tools 10 at various simultaneous depths do not necessarily have to be adjacent one another. But the closer together, the closer the three different spectral acquisitions will be to the same soil.

System

By additional reference to FIGS. 7-10, embodiments of a system according to aspects of the invention are illustrated. Such an overall system could include use of tool(s) 10 described above.

FIG. 7A diagrammatically illustrates a tractor 30 pulling a toolbar frame 32. A front tool bar has two tools 10 mounted in operative position. A back tool bar has a plurality of injection knives 36 with supply tubes operatively connected to a follow-along anhydrous tank/trailer 35. In this configuration, one or both tools 10 could be operated to produce nitrate level predictions as the system moves through a field. Those predictions could be immediately utilized to modulate fertilizer application. As indicated, even a single tool 10 might be used as an approximation of nitrate levels but multiple injection knives operated to cover a substantial working application width. Alternatively, the ratio of tools 10 to number of knives 36 could be smaller so that modulation of fertilizer application could more closely follow the predictions of the tools 10.

FIG. 7B illustrates several different styles of nitrogen fertilizer applicators, some for liquid and some for solid fertilizers. Such are well-known in the art. See also www.pioneer.com/CMRoot/Pioneer/US/Non_Searchable/agronomy/cropfocus_pdf/nitrogen_fertilizers_stabilizers.pdf-and yara.com/products_services/fertilizers/product_portfolio/field_applied, incorporated by reference herein, with information about both types.

Alternatively, one or more tools 10 could be operated through a field in a first pass and essentially map the field for nitrate levels to high spatial resolution. In a second pass, fertilizer could be applied, modulated by that map following that high spatial resolution.

FIGS. 10A and B diagrammatically illustrates one form of tool 10' and 10". Commercially available Agilent 4100 diamond ATR-FTIR ruggedized spectrometer 6'/7' has a size and weight (see www.agilent.com/cs/library/brochures/5990-8097EN_4100-Exoscan-FTIR-Brochure.pdf incorporated by reference herein) that could fit on an approximately 1 to 2 foot long by 2 to 8 inches wide by ½ to 1 inch thick flattened steel base 4, extend diamond ATR cell 7'/8' through a complementary diameter through-hole in base 4, and encase the combined ATR and FTIR components 6'/7'/8' in housing 5. These dimensions can, of course, vary according to need or desire. Alternate commercially available spectrometer 6" is shown in FIG. 10B with tool 10" and ATR/diamond 7"/8".

Figure 12:
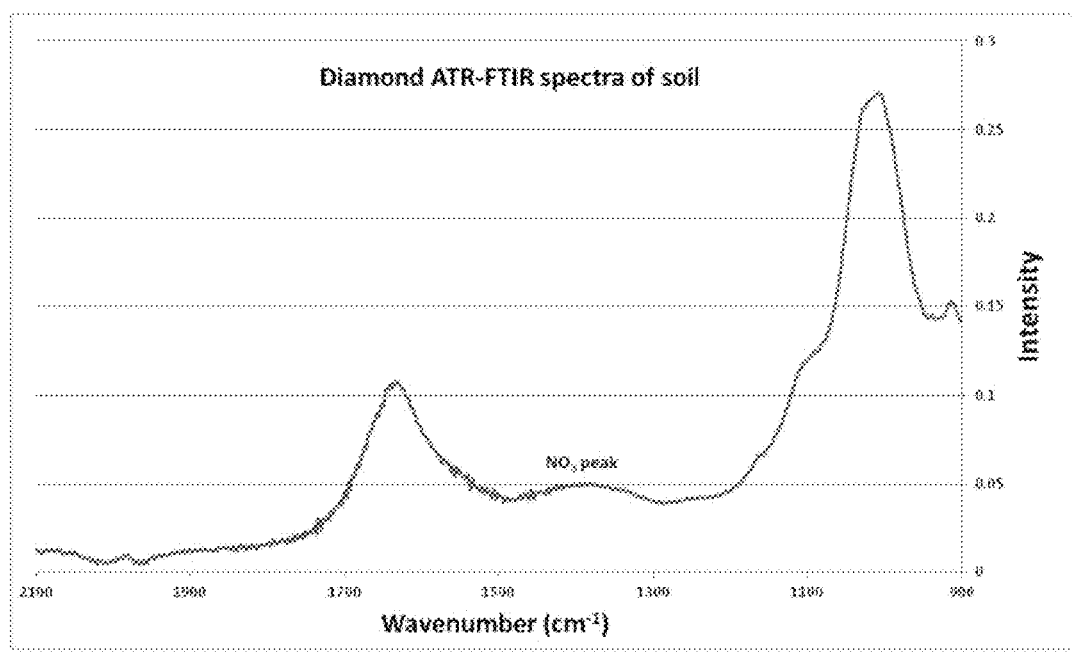
FIG. 12 is a graphical representation of an example of spectra obtained with one version of the sensing tool of FIG. 11. The nitrate peak is marked.
Figure 13:
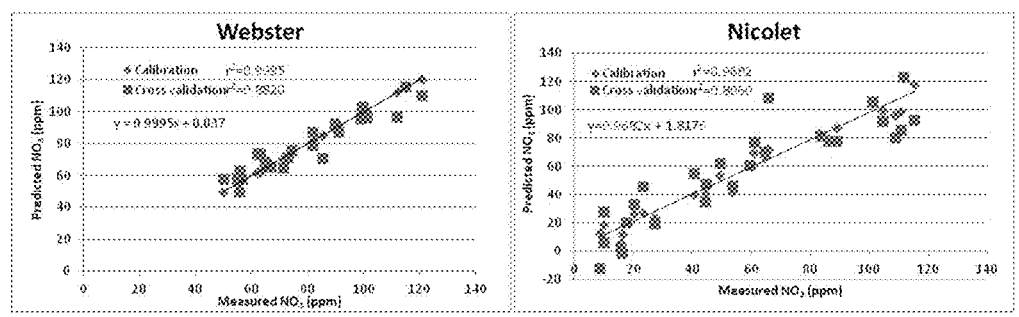
FIG. 13 is a pair of graphs illustrating correlation of nitrate level predictions from the sensing tool of FIG. 11 versus nitrate level measurements by alternative methods.

With further reference to FIGS. 11-13, additional discussion of the over-all system is as follows.

The intended application for the soil nitrate sensor system is to use the data to spatially modulate soil nitrogen fertilizer applications in corn fields and various other crop production systems.

An innovation is a sensor system that is capable of measuring soil nitrate levels in agricultural fields in real-time and on-the-go. The system can be used for precision application of nitrogen fertilizer in agricultural fields either in two operations (first measure soil nitrate levels and then apply the nitrogen fertilizer based on the results) or in a single operation (the soil nitrate sensor is integrated with a nitrogen fertilizer applicator) such that sensor readings are used to modulate nitrogen fertilizer application rates in-real-time and on-the-go as nitrogen fertilizer is being applied.

In addition to the components shown in FIG. 11, the system can also include a computer, cables, power supply and a global positioning system (GPS). Data acquired from the D-ATR-FTIR spectrometer are transferred to the computer and interpreted by software algorithms. During operation GPS coordinates are also continuously received and recorded along with the FTIR spectra.

Figure 8:
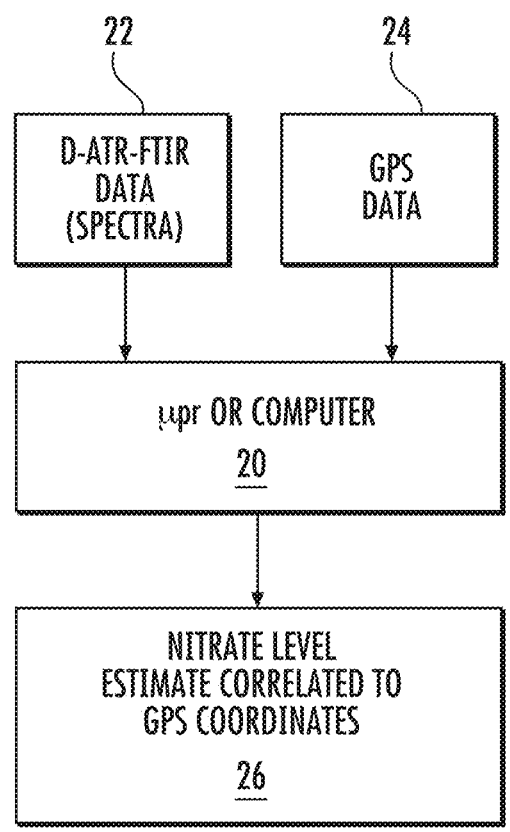
FIG. 8 is a block diagram of data handling by a system according to an exemplary embodiment of the invention.

As illustrated in FIG. 8, the D-ATR-FTIR data 22 can be processed by computer 20 remote from tool 10 (e.g. in a tractor cab) and a nitrate level prediction correlated with georeferencing 24 obtained from a GPS 33 (e.g. also on the tractor). The system can then output the georeferenced nitrate predictions 26 for further use (e.g. immediate fertilizer application modulation or a second pass fertilization application modulation). It is to be understood that the georeferencing might be available from existing or other GPS components (e.g. such as might be in place in a tractor precision farming intelligent controller).

Consistently achieving good contact between the diamond and the soil surface can be important or critical and one way it can be achieved is by having a slight backward pitch on the shank base so that the soil is continuously being compressed below the shank base as the sensor shank is pulled forwarded through the soil. The depth at which the shank base is pulled through the soil can be held constant or continuously varied (up and down) so as to obtain average soil nitrate readings over a given depth range.

Examples of how the system can produce the nitrate predictions are set forth below.

Methods

In one aspect of the invention, measurements obtained by tool 10 are processed in certain ways. This can include both what measurements are used and then how they are processed.

In particular, in one embodiment, measurements are informed by the LSNT protocol, discussed above, and processing of the measurements is according to a particular algorithm. These will be discussed in the Examples below. The Examples also demonstrate proof of concept for aspects of the invention.

Estimating the potential economic value of the invention requires several major assumptions. First, it is necessary to estimate the magnitude of improvement in nitrogen use efficiency in corn production, i.e. how much less total nitrogen fertilizer a farmer can apply without loss of yield. To do so, we look to the work of Jaynes et al. (2004) who implemented the LSNT on a watershed scale and reduced nitrate loss by ~30% relative to fall applied N fertilizer (current dominant framer practice), which implies a 30% increase in nitrogen use efficiency. Similarly, Bausch and Diker (2001) reported that in-season variable rate N fertilizer applications based on crop canopy sensing reduced the amount of N fertilizer needed to obtain comparable maize yields by 39.2 kg ha$^{-1}$, about a 20% improvement in nitrogen use efficiency. Currently 50 to 70% of the nitrogen fertilizer applied on Iowa corn fields is lost to leaching, volatilization, and/or denitrification. Indeed, Cassman et al. (2002) estimated that on average just 37% of the applied N fertilizer is actually used by corn in the north central U.S. Based on the above, we estimate that precision application of nitrogen fertilizer based on high density geospatially registered soil nitrate data using the LSNT protocol has the potential to reduce the amount of nitrogen fertilizer required to achieve comparable yields by 10 to 50% relative to current practices. The savings relative to spring applied N fertilizer using a split application (current best management practices or BMP) will be less but should also be significant due to the capacity to spatial distribution fertilizer where it is needed within fields. The second assumption is the extent to which this technology will be adopted. U.S. farmers spend more than $8 B annually on nitrogen fertilizer, including about $1 B annually spent by corn farmers in Iowa. If the system is fully successful, the potential savings to farmers by improving nitrogen use efficiency is easily in the $100s M annually in Iowa and greater than $1 B annual at a national scale. Depending on the extent of adoption, a significant fraction of this annual savings could be captured by manufacturers, distributors and consultants building, marketing and deploying the soil nitrate sensor system. Furthermore, nitrate pollution of surface and ground water in the upper Mississippi valley including Iowa is a major environmental issue, and the US-EPA has required Iowa to reduce nitrate loading of the Mississippi-Missouri river system by 45%. If widely implemented, the invention has the potential to significantly help Iowa and other states meet the EPA mandate.

Example 1

The following discussion gives context to the genesis and development phases which have or will occur with the invention and its aspects and, in particular, to the variety of factors and considerations that can be involved in providing a technical solution to the problems in the state of the art identified and addressed by the inventors.

Phase 1: The purpose of the Phase 1 study is to determine whether or not it is possible to measure soil $NO_3^-$ concentrations with sufficient accuracy using the Agilent 4100 Exoscan FTIR Spectrometer with the diamond ATR accessory. The scope of this laboratory study will involve 5 different soil types amended with $KNO_3$ to achieve approximately 0, 25, 50, and 100 mg kg$^{-1}$ $NO_3^-$ concentrations. Analyses will be run with samples prepared at three different soil moisture levels to assess the impact of soil moisture on the accuracy of soil $NO_3^-$ concentration predictions. Sample presentation with the ATR system will be both static and dynamic. Various data processing techniques such as the partial least squares regression will be used to relate the spectra to soil $NO_3^-$ concentrations measured independently for the samples using the microplate method. The data analysis will include spectral masking to simulate a less expensive filter spectrometer system.

Phase 2: The prototype system will consist of a steel shank, an instrument housing assembly attached to a toolbar, a hydraulic or mechanical system for raising and lowering the shank, the FTIR spectrometer, a GPS system, and a computer for external control of the spectrometer and data acquisition. A diamond ATR cell will be embedded in the bottom of the shank for presentation to the soil. The system will be designed such that the pitch of shank can be adjusted to control compression of the soil against the diamond ATR cell when the shank is moving forward through the soil. On completion the prototype will be field tested for ruggedness and the ability to acquire soil FTIR spectra.

Phase 3: Performance of the prototype field mobile $NO_3^-$ sensing under field conditions will be evaluated. The envisioned work will include assessing mechanical and instrument performance and possible upgrading of the system, calibration of the prototype sensor system under field conditions, and performance testing to quantify the agronomic and environmental impact of using the field mobile $NO_3^-$ sensing technology for precision application of nitrogen fertilizer.

Example 2

The basic data obtained are D-ATR-FTIR spectra of the soil. An example of a soil D-ATR-FTIR spectra is shown in FIG. 12. This spectra was obtained by pressing a D-ATR-FTIR spectrometer into a soil by hand. The nitrate peak is evident in the spectra as a broad hump between 1300 and 1500 cm$^{-1}$.

Several chemometric steps are used to estimate soil nitrate concentrations from the D-ATR-FTIR spectra. During a field operation individual spectra are acquired in less than 1 second, hence during operation a continuous stream of spectra will be uploaded to the computer. The data can either be stored and processed later, or processed in-real-time. One example of basic steps that can be used to process the data include: 1) filtering the data to throw out unacceptable spectra, 2) normalization which involves subtracting the mean and dividing by the standard deviation of intensity values for each wavenumber obtained from a calibration set of spectra, 3) averaging several contiguously collected filtered and normalized spectra, and 4) using a partial least squares (PLS) regression model to predict soil nitrate concentrations. The PLS regression model is developed by collecting D-ATR-FTIR spectra and measuring KCl extractable nitrate for a large and diverse group of soil samples.

Figure 9:
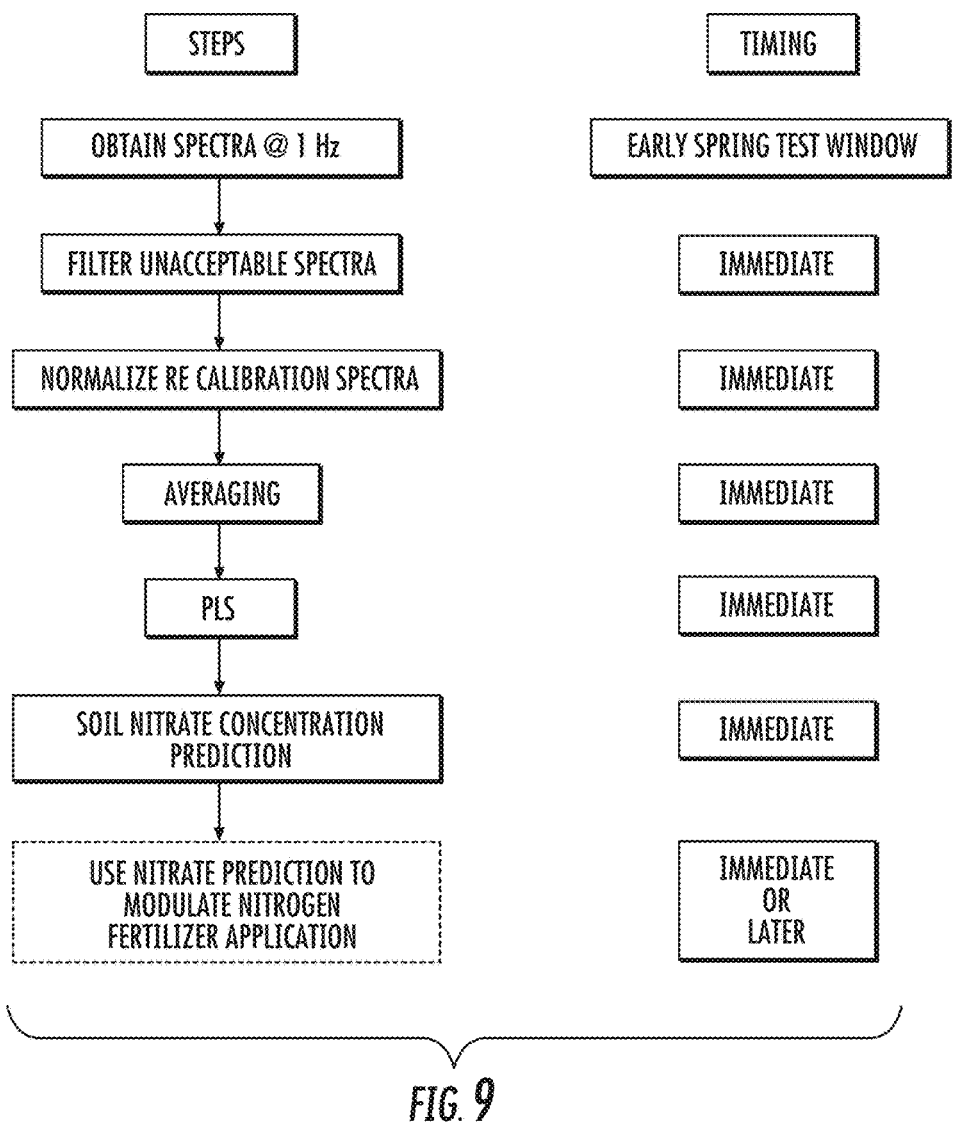
FIG. 9 is a flow chart of one embodiment of an algorithm for processing spectra obtained by the sensing tool according to one exemplary embodiment of the invention.

FIG. 9 is a flow chart of the steps described above. They can be implemented in a computer having relatively standard processing capabilities. Or it can be an existing, on-board precision farming processor, such as are commercially available. It can be configured to communicate with the FTIR spectrometer, have sufficient digital storage for high resolution nitrate estimates across the field, as well as sufficient calibration models, and processing power to meet almost real-time nitrate predictions.

In the method of FIG. 9, the frequency of collection of spectra can vary according to the designer's or user's desire or need.

The filtering step promotes elimination of irrelevant data. Or it could simply reject data that does not pass some test. An example of such test involves the following data processing steps starting with a raw spectra for an unknown sample: 1) For each wavenumber in a spectra, the intensity value is subtracted from the average intensity for that same wavenumber obtained from a calibration set, this deviation is then squared. 2) The sum of such squares for all wavenumbers in the unknown spectra is compared with a threshold value; if the sum of squares for the unknown spectra is large than the threshold value, then the unknown spectra is discarded, if sum of squares is less than the threshold value then the unknown spectra is retained. 3) Threshold values are chosen to exclude a fraction (example 5%) of all unknown spectra.

The normalizing procedure is used to weight all portions of the spectra equally and is done only for unknown spectra that have passed the initial filtering test described above. For each wavenumber the mean intensity for that wavenumber from the calibration set is subtracted from the intensity of the unknown spectra at that wavenumber and then divided by the standard deviation for that wavenumber obtained from the calibration set. The product is a normalized (transformed) spectra for the unknown sample.

The normalized spectra are truncated by removing all wavenumbers larger than an upper specific value and lower than a low specific value. For example, all wavenumbers larger than 2008 $cm^{-1}$ and smaller than 929 $cm^{-1}$ might be eliminated. The optimum wavenumber range or rangers retained in the truncated normalized spectra might vary, however the 2008 to 929 $cm^{-1}$ range has been shown to be effective and was used to generate the results shown in FIG. 13.

During field operation a new spectra will be collected approximately every second as the tool moves through the field. To integrate over depth, the tool will be continuously raised and lowered thus a set of contiguously collected spectra will represent a certain distance along a transect within the field and different depths within the soil. Multiple contiguous normalized and truncated spectra will be averaged by summing the intensities at each wavenumber and dividing by the number of spectra being averaged. The average truncated normalized spectra will represent soil along a discrete transect and for the range of depths being analyzed. As will be appreciated, however, by those skilled in this technical art, variations to the foregoing methodologies and techniques are possible.

A multi-variant statistical model (such as can be derived using partial least squares regression, principal components regression, artificial neural network, genetic algorithm, etc.) is then utilized to analyze an average truncated normalized spectrum to estimate the concentration of $NO_3^-$ in the soil volume represented by that averaged truncated normalized spectrum. The multi-variant statistical model must be built and calibrated in advance using spectra and independently measured soil $NO_3^-$ concentrations from a calibration set of soil samples that should represent the full diversity of soil properties found in the field being analyzed.

As can be appreciated, and as is discussed in (Cheng-Wen Chang (2001), (Cheng-Wen Chang (2002) and (Jones 2013), each which is incorporated by reference herein, a variety of data pre-processing procedures (such as the filtering, normalizing and averaging procedures described above), multivariate statistical model development procedures, and model calibration of methods are possible. The key point here is that these are mathematical treatments of the soil mid-infrared spectral data that are used to predict soil $NO_3^-$ concentrations for the purpose of precision management of nitrogen fertilizer applications.

The result is an estimation or prediction of nitrate level based on a matching or correlation to a calibration or reference model or models.

FIG. 13 shows two examples of the relationship between measured and predicted soil nitrate concentrations obtained using a D-ATR-FTIR system inserted directly into samples of Webster and Nicolett series soils (see soilseries.sc.egov-.usda.gov/osdname.apx, incorporated by reference herein).

The relationship between measured and predicted soil nitrate concentrations for samples of Webster and Nicolet soil are shown. The predictions were made using a PLS model and D-ATR-FTIR spectra of the soils. Various amounts of nitrate were added to the soil samples, the samples were thoroughly mixed, scanned with the spectrometer, then KCl extracts of samples of each soil were analyzed for nitrate using a microplate reader.

These results were the first successful tests of the D-ATR-FTIR system and include only two soil types and cover only a narrow range of soil moisture. Additional research expanded the number of soil types and increased the range of soil moisture levels. The research is designed to further verify the capability of the D-ATR-FTIR system and to assess the transferability of calibrations form one soil type to another and across a range of soil moistures. Work is also underway to develop computer software to automate the calibration and analysis process and to design and build a shank prototype for field testing.

Figure 14:
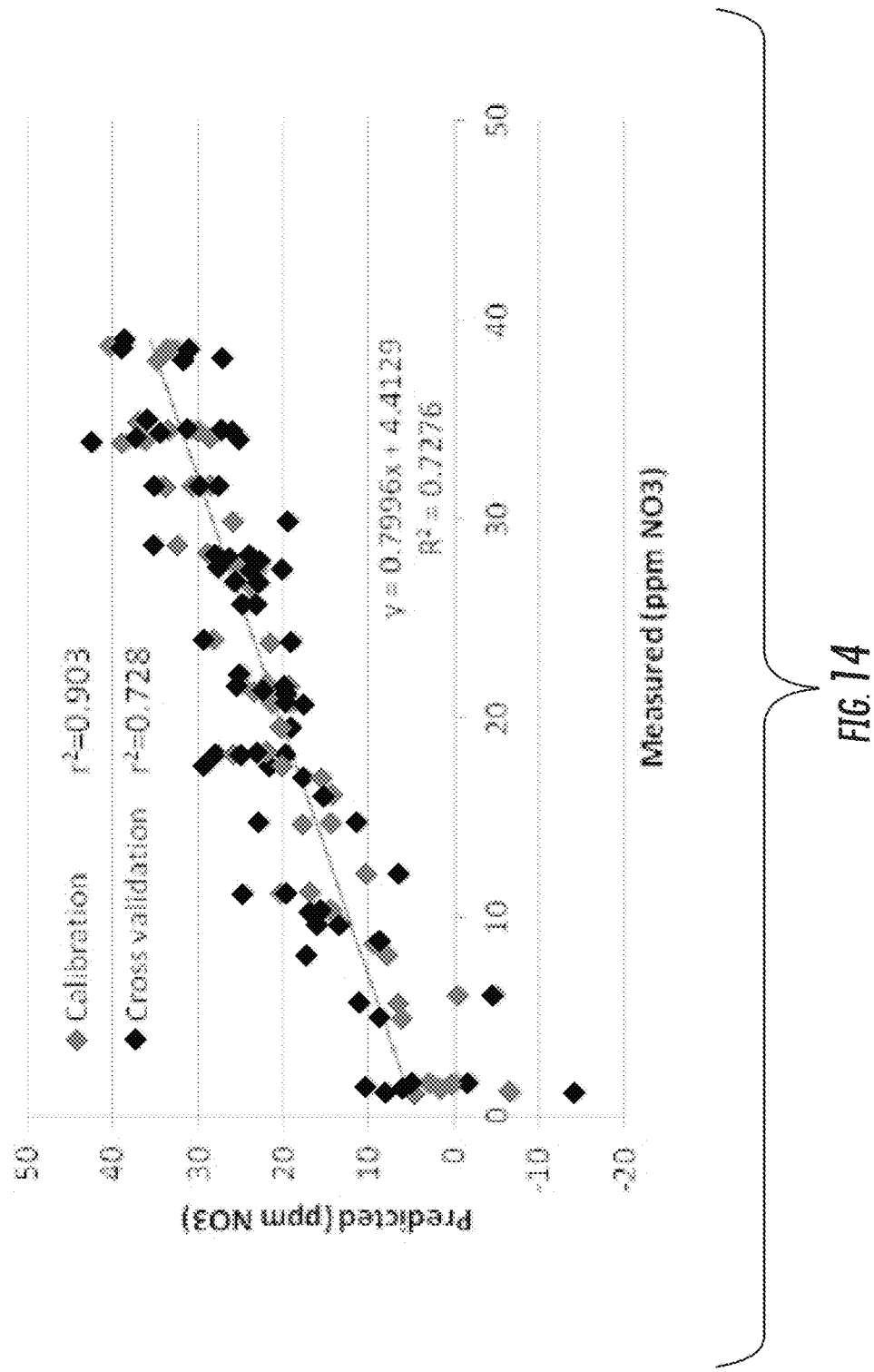
FIG. 14 is another example of a graph illustrating validation of the apparatus and methods according to aspects of the present invention.

FIG. 14 shows results for a second test of the hand held D-ATR-FTIR system for measuring soil nitrate concentrations. The test includes 5 soils (Webster, Nicollet, Okoboji, Exira and Hanlon soil series) with textures ranging from fine sandy loam (Hanlon) to silty clay loam (Okoboji) and soil organic C concentrations ranging from 0.5% to 5%. This data set includes the full range of textures and organic matter found in Iowa soils (no calcareous soils are included, because calcareous soils are anticipated to be problematic). Pooling data from these diverse soils, we were still able to build a multivariate partial least squares (PLS) regression model that predicts soil $NO_3^-$ concentrations with sufficient accuracy ($r^2$=0.728 for cross validation) to divide agricultural soils into three working groups: soils that need no additional N fertilizer, soils that need a moderate amount of N fertilizer, and soils that need a large amount of N fertilizer based on the LSNT protocol. We anticipate being able to substantially improve the accuracy of soil $NO_3^-$ predictions from the results shown in FIG. 14 by further optimizing the chemometrics such as including soil moisture as a co-variate in the multivariate statistical model and by optimizing the wavenumber range used during the truncation of the normalized spectra.

Example 3—Field Studies

Development of Field Mobile Soil Nitrate Sensor to Facilitate Precision Fertilizer Management The Late Spring Nitrate Test (LSNT), also known as the pre-side dress nitrate test (PSNT), is an established tool for N fertility management in corn production. Although shown to be effective for improving NUE (nitrogen uptake efficiency) and reducing $NO_3^-$ leaching losses, the LSNT is not widely used by farmers, because of its cost, low spatial resolution, and the time delay between soil sampling and the availability of a N fertilizer prescription increases risk for farmers. The overall goal of our research is to develop soil $NO_3^-$ sensor technology that can be attached to farm implements and used to determine in-real-time on-the-go soil $NO_3^-$ concentrations with sufficient accuracy to facilitate precision application of nitrogen fertilizers. We used diamond-attenuated total internal reflectance (D-ATR) Fourier Transform Infrared (FTIR) spectroscopy as the basis for the soil $NO_3^-$ sensor system. We were successful in developing methodology for collecting soil spectra with an Agilent 4100 Exoscan FTIR Spectrometer from 5 soil types amended with different quantities of $KNO_3$ and processing collected data using partial least squares regression analysis. Cross validation $r^2$ (predicted vs. actual $NO_3^-$ concentrations) for pooled data was 0.73, suggesting great potential of utilizing the Exoscan FTIR Spectrometer for soil $NO_3^-$ determination. Currently we are analyzing spectra of the soil samples collected from four agricultural fields to encompass variation in soil characteristics.

Background

There is an enormous need to improve nitrogen use efficiency (NUE) in agricultural production. Our goal is to develop infield, on-the-go, soil $NO_3^-$ sensor technology that will both support real-time modulation of N fertilizer rates and generate high spatial resolution soil $NO_3^-$-data. Soil $NO_3^-$ levels can easily be measured in a laboratory, but until now direct field-mobile spectroscopic techniques for measuring soil $NO_3^-$ levels have not been possible. Nitrate does not adsorb light in the visible and near infrared regions of the electromagnetic spectrum, but does adsorb light in the mid-infrared region. Our key innovation is to use a new, small, mobile, and robust Fourier Transform mid-InfraRed (FTIR) spectrometer equipped with a Diamond-Attenuated Total Internal Reflectance (D-ATR) sample cell to measure soil $NO_3^-$ levels. This study was conducted to test whether D-ATR-FTIR is effective for measuring soil $NO_3^-$ levels in the critical range (0-100 ppm).

Equipment

Figure 15:
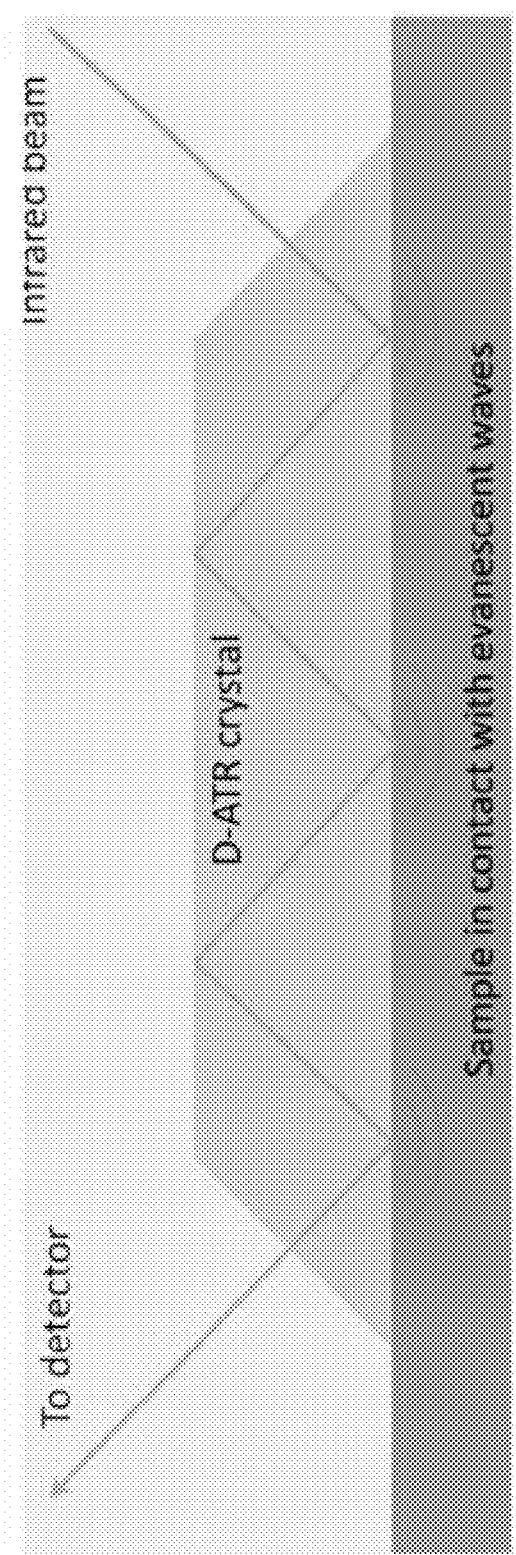
FIG. 15 is a greatly enlarged scale diagram of a D-ATR crystal illustrated ATR concepts.

Attenuated total reflection (ATR) is a sampling technique that enables solid or liquid samples to be analyzed by FTIR directly without sample preparation. ATR is typically an attachment to an infrared spectrometer such that light is directed toward a crystal of high refractive index that is transparent to the infrared radiation (light). The optical surface is one of the crystal facets that is placed in direct contact with a sample. Any light that impinges on the optical surface from within the crystal at an angle less than the "critical angle" will be reflected back into the crystal as long as the material in contact with the optical interface (the sample) has a lower refractive index. See diagrammatic depiction at FIG. 15.

However, the evanescent wave moving across the optical surface of an ATR cell is partially attenuated by interaction with a sample in direct contact with the optical surface, thus creating an absorbance spectra of the sample.

Spectra

Figure 16:
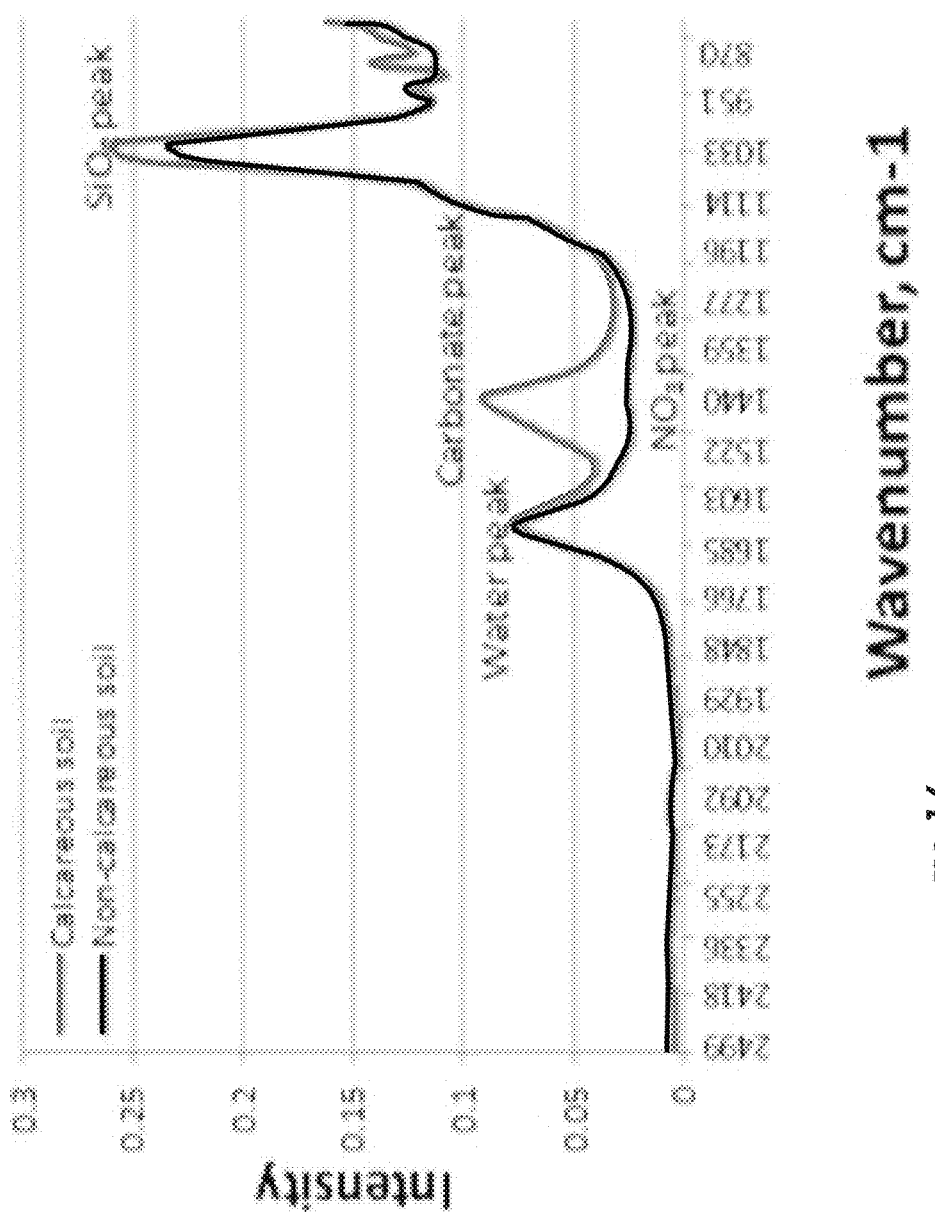
FIG. 16 is a graph related to spectra obtained during field testing of an embodiment of the invention.

In the example spectra shown in FIG. 16, the presence of the water film is evident by the prominent O—H bending band for water at ~1670 $cm^{-1}$, soil mineral particles touching the diamond are evident by the Si—O stretching band at ~1000 $cm^{-1}$, and $NO_3^-$ in the soil water is indicated by the weak N—O stretching band at ~1400 $cm^{-1}$. Although the nitrate band is small (because nitrate concentration is only 42 ppm in this soil), we are still able to observe the $NO_3^-$ peak.

Summary of Findings

Figure 17:
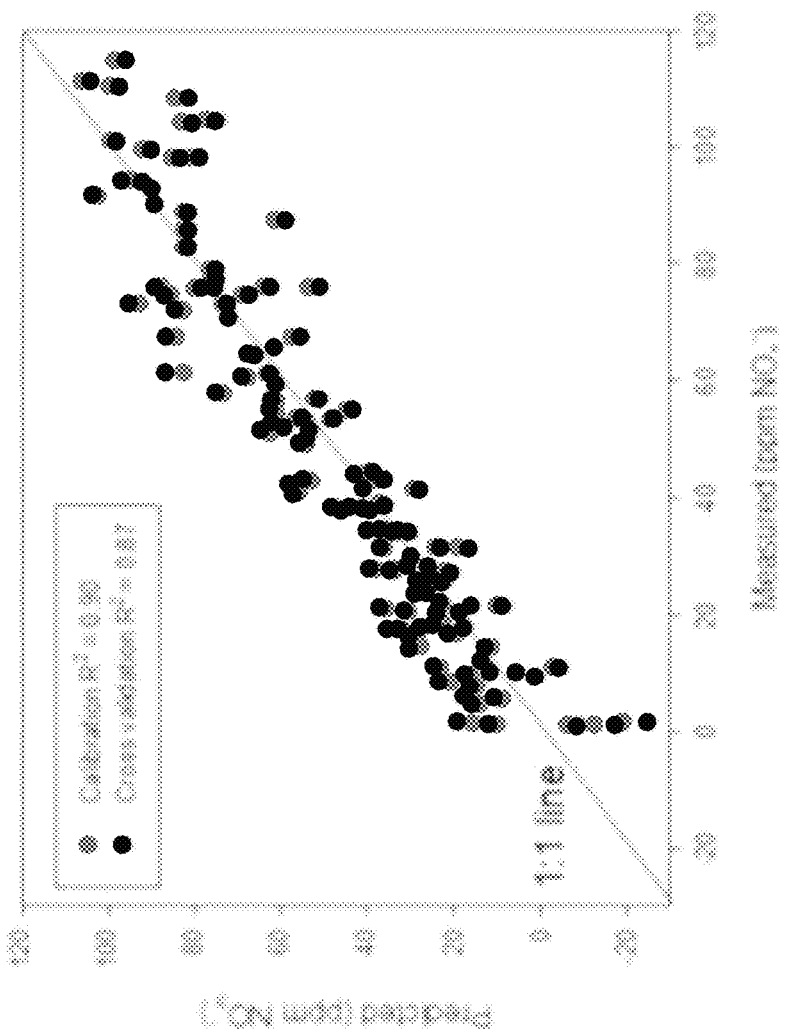
FIG. 17 is a graph related to the field testing showing correlation of measured (by another method) to predicted (according to the present invention) nitrate concentrations.

Laboratory calibration: 0 to 100 mg $L^{-1}$ of $KNO_3$ was added to 5 soil types that varied in texture and SOM, soil was equilibrated at typical field soil moisture levels, and the D-ATR-FTIR was pressed directly into the soil subsamples to collect spectra. The subsamples were extracted with 2 M KCl and the extracts analyzed $NO_3^-$ the same day using a standard colorimetric procedure. The D-ATR-FTIR spectra were related to the measured soil $NO_3^-$ levels using partial least squares regression, a traditional multivariate chemometric procedure. See FIG. 17.

Figure 18:
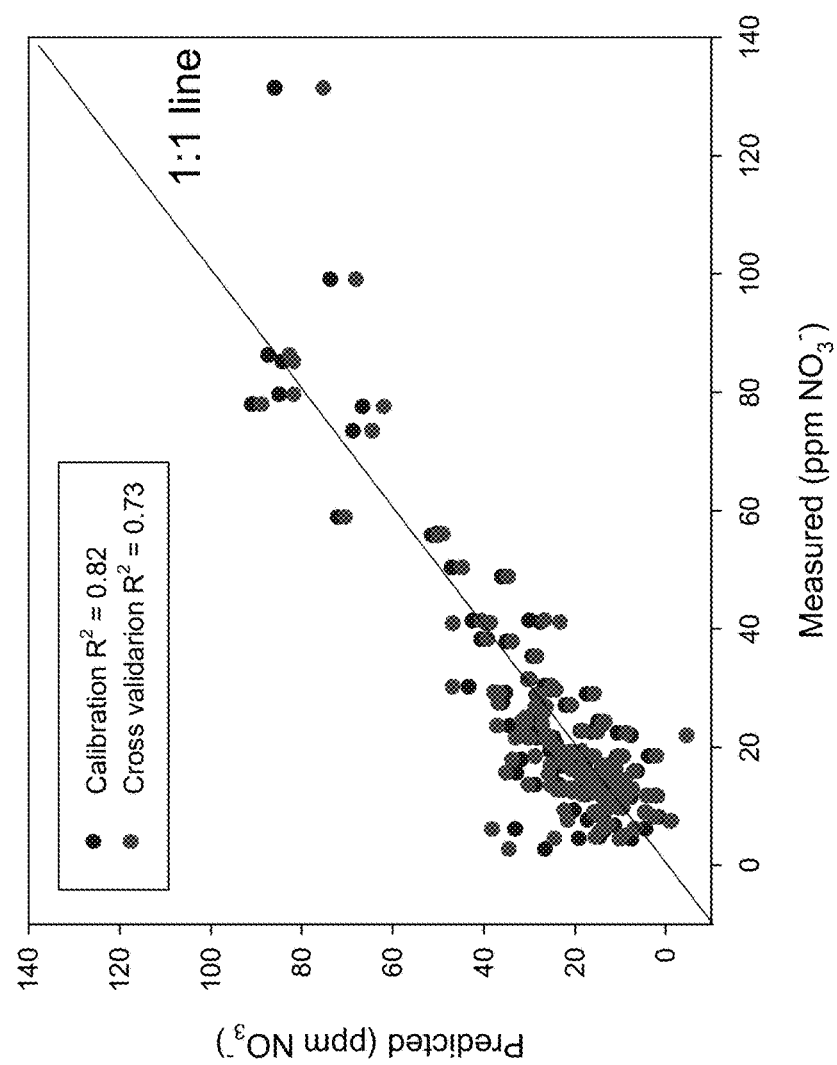
FIG. 18 is a graph related to the field testing showing correlation of measured (by another method) to predicted (according to the present invention) nitrate concentrations. The relationship between soil nitrate concentrations predicted using an Agilent 4100 ExoScanD-ATR-FTIR spectrometer and measured by a standard analytical method. The pooled data for soil samples was collected from four agricultural fields in the late Spring of 2016.

Field data set: A total of 124 soil samples were collected from four agricultural fields (1.2 to 12.2 Ha) during late May-early June 2016. Samples were scanned using the Agilent 4100 ExoScan D-ATR-FTIR spectrometer and analyzed for KCl extractable $NO_3^-$ within 24 hours of collection. The D-ATR-FTIR spectra were related to the measured soil $NO_3^-$ levels using partial least squares regression. See FIG. 18.

Figure 19:
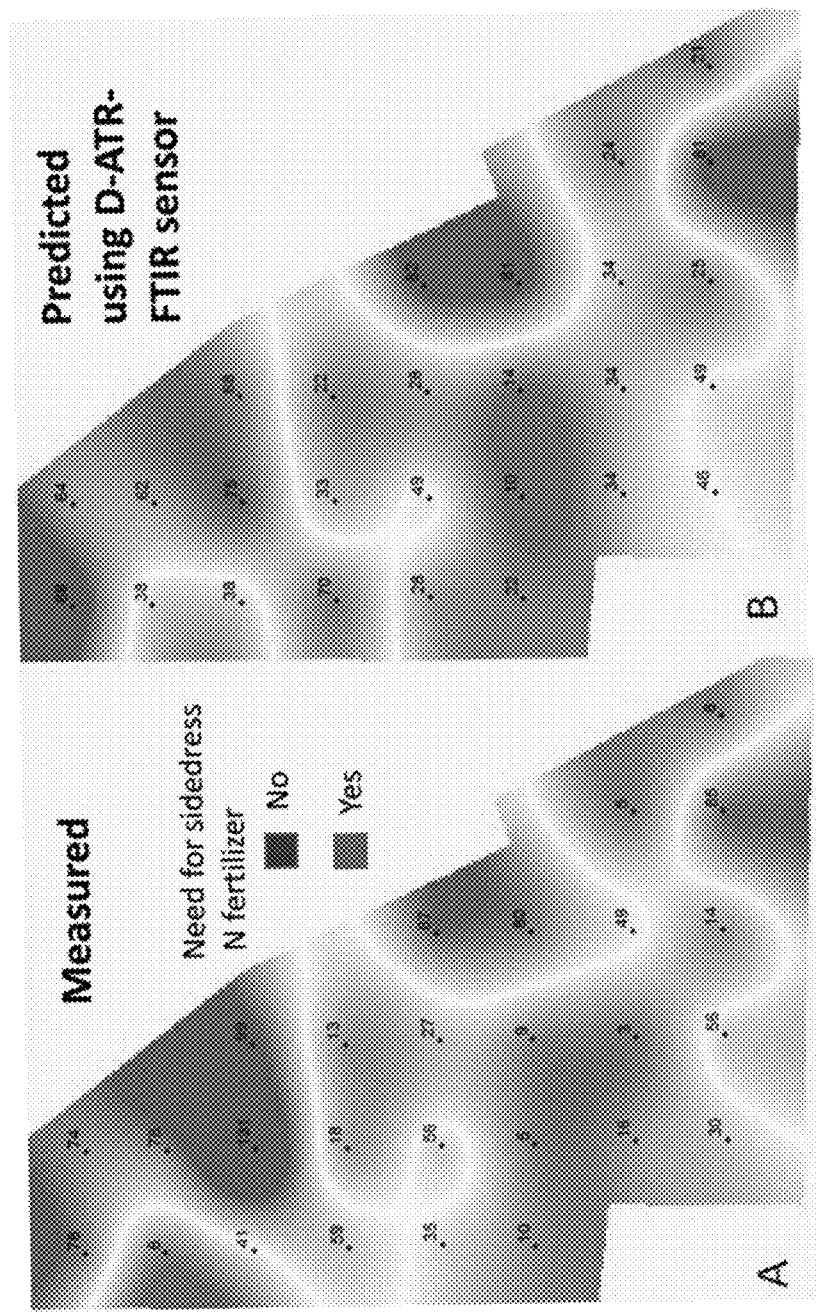
FIG. 19 are maps showing from the field testing spatial relationships between areas needing side dress N fertilizer and those that do not. The map on the left is measured (by another method) while on the left is predicted (according to the present invention). Ma showing spatial relationships between areas needing sidedress N fertilizer (Blue) and areas not needing sidedress N (Red) for a 30 Ac agricultural field in central Iowa. The man on the left (A) is based on laboratory measured soil nitrate concentrations: the map on the right (B) is based on soil nitrate concentrations predicted using the D-ATR-FTIR sensor. Numbers are measured or predicted nitrate concentrations ($NO_3^-$ in mg $kg^{-1}$). Note: white lines show boundaries between blue and red areas.

Maps showing spatial relationships between areas needing sidedress N fertilizer (Blue) and areas not needing sidedress N fertilizer (Red) for a 12.14 Ha agricultural field in central Iowa. The maps were generated using ArcGIS software using a spline with barriers—raster interpolation technique. The map on the left (A) is based on laboratory measured soil $NO_3^-$ concentrations; the map on the right (B) is based on soil $NO_3^-$ concentrations predicted using the D-ATR-FTIR sensor. Numbers are measured or predicted $NO_3^-$ concentrations in ppm. See FIG. 19.

Results of preliminary studies conducted using an Agilent 4100 ExoScan D-ATR-FTIR system, demonstrate the potential of D-ATR-FTIR spectrometers to predict soil $NO_3^-$ concentrations within the range needed for precision N fertilizer management.

Field Studies

We tested the performance of the hand-held Agilent FTIR ATR spectrometer on samples collected from four agricultural fields in central Iowa. This was done to determine whether or not the system has enough accuracy to predicting soil nitrate concentrations for sample collected from agricultural fields at the time (late spring) when sidedress nitrogen fertilizer is typically applied. This test was as close as possible to an actual application of the system short of having a real time mobile nitrate sensor prototype.

The work done: Four fields, 10 to 30 acres in size, were sampled. Two fields were in a corn-soybean rotation, while the other two fields were in continues corn. About 30 samples per field were collected in a grid pattern to a depth of ~15 cm during late May-early June 2016 when the corn plants were ~15 cm tall. The soil samples collected from the four fields had a wide range in soil moisture, organic matter, texture and other chemical and physical properties. Location of each sample was georeferenced using Trimble GPS unit. Soils samples were brought to the laboratory, scanned using the Agilent FTIR ATR spectrometer and then analyzed for nitrate using a standard reference method (extract the sample with 2M KCl and then analyze the extract for nitrate using a colorimetric procedure) within 24 hours of sample collection. Soil moisture content and pH were also measured for all samples. The D-ATR-FTIR spectra were related to the measured soil nitrate levels using partial least squares regression. The relationship between predicted and measured soil nitrate concentrations pooled across all four fields is presented in FIG. 18.

Maps of measured and predicted nitrate concentrations were generated using ArcGIS software and interpolated by means of a spline with barriers—raster interpolation technique.

Maps showing spatial relationships between areas needing sidedress N fertilizer (Blue) and areas not needing sidedress N (Red) for a 30 Ac agricultural field in central Iowa. See FIG. 19. The map on the left (A) is based on laboratory measured soil nitrate concentrations; the map on the right (B) is based on soil nitrate concentrations predicted using the D-ATR-FTIR sensor. Numbers are measured or predicted nitrate concentrations ($NO_3^-$—N in mg $kg^{-1}$).

Software development: Until now we have been using a commercial chemometric software program (The Unscrambler) to perform partial least-squares (PLS) regression, which is used to develop a model that relates the D-ATR-FTIR spectra to measured soil nitrate concentrations. We have developed and validated a new software tool for partial least-squares (PLS) regression. The new software tool has been shown to give comparable results to the commercial software but is based on open source algorithms and therefore is independent of commercial software. This new software will ultimately be part of the software package needed to run the commercial system. In addition to PLS, we are building into the new software algorithms for prescreening spectra to discard outliers and to transform the spectra prior to PLS analysis. Spectral screening and transformations prior to PLS analysis are key to the success of this embodiment.

Options and Alternatives

As will be appreciated by those skilled in the art, the invention and its aspects can take many forms and configurations. The embodiments given above are by example only, and not by limitation. Variations obvious to those skilled in the art are included with the invention.

The following are further examples of options and alternatives:

Tool 10

Different soil openers are possible. Likewise there could be soil closers that follow base 4. The base 4 can vary in form factor and configuration. The structure to mount tool 10 to a tool bar or frame can vary, as can the technique to adjust pitch and/or depth.

Soil Opener

Figure 20:
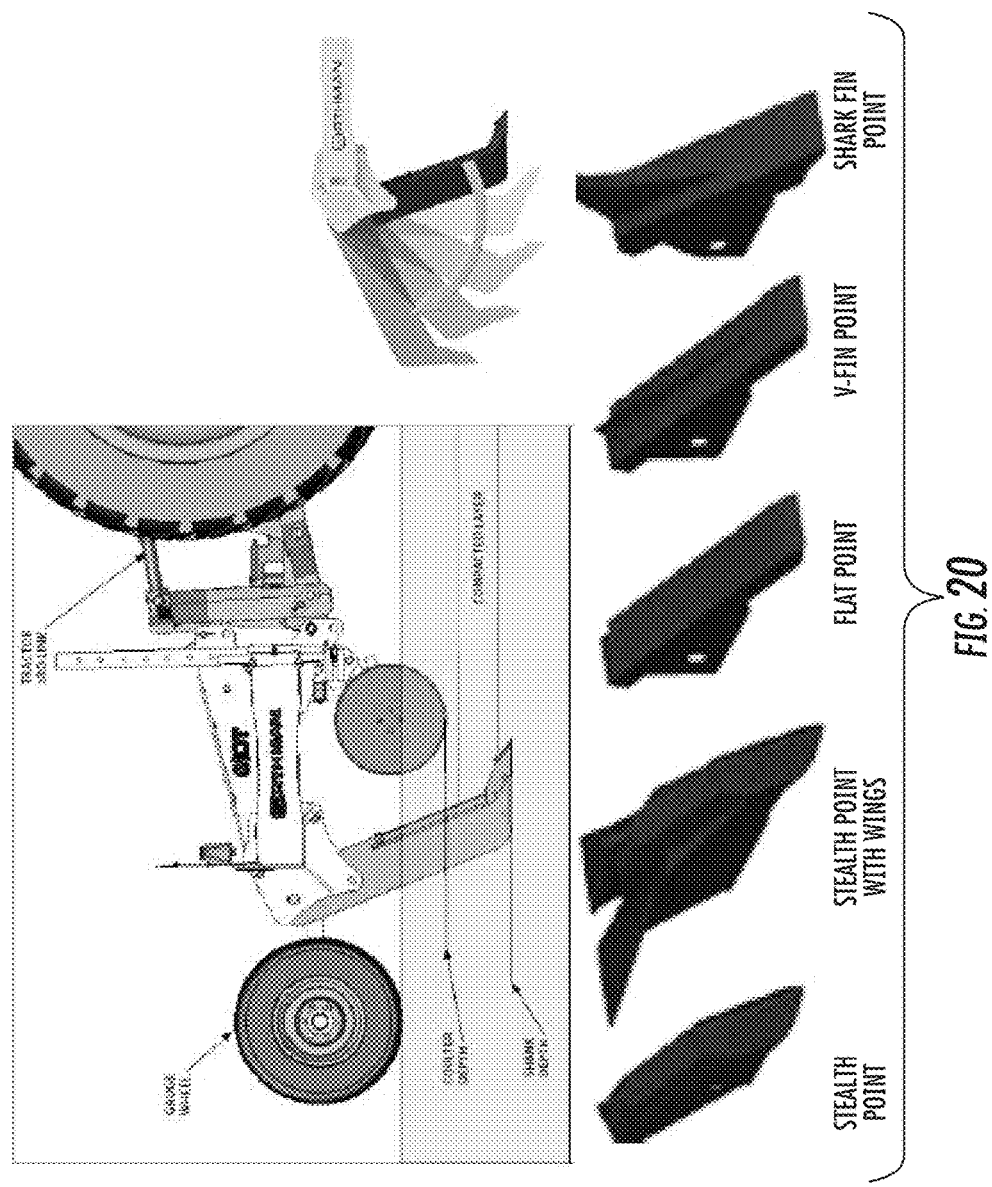
FIG. 20 are diagrams of one example of a type of soil opener that could be used with embodiments of the invention, as well as one example of a tractor and actuation system to support the tool and adjust pitch and depth of the tool.

For example, soil opener 3 could have the basic form factor of previously mentioned commercially-available Model 6/DT Subsoil Ripper (which has a variety of possible point options. See www.orthman.com/Userfile/manuals/Subsoil-Riper-Manual-(125-027-01).pdf, incorporated by reference herein. As illustrated in FIG. 20, such a soil-working tool can be mounted to a tool bar or other structural support pulled by a tractor. Both depth and angle relative the ground can be adjusted. Embodiments of the invention would add shank base 4 and the other components of FIG. 11. The combination can be pulled through the field and spectra acquired.

Pitch and Depth

As will be appreciated by those skilled in this technical area, the precise way in which pitch and depth are adjusted can vary. In one example, hydraulic actuators can swing the shank 2 (as diagrammatically illustrated in FIG. 20) to adjust pitch, while another hydraulic actuator could raise or lower the entire tool to adjust depth. The system could be calibrated so that certain pre-designed pitches and depths could be set from the tractor. Alternatively, there could be mechanical adjustments to set pitch or depth as desired. For example, there could be visual markings on the tool that are calibrated to certain pitch angles. The operator would adjust shank 2 to match those markings. There could also be one or more mechanical stops that allow the operator to manually set the pitch or operate the actuator that changes pitch until that mechanical stop is reached. Still further, there could be one or more sets of holes in shank 2 and other structure that allows the operator to place a pin to manually set pitch. The operator could also simply manually measure the angle of the soil opener 3 and a reference to manually set pitch before the tool is used. Other types of actuators are possible, including electrical, electromechanical, or mechanical.

Pitch during operation can be selected according to desire or need. As mentioned above, it can be quite small (e.g. a few degrees) to balance the promotion of soil-to-diamond contact while moving without unreasonable amount of drag. It is believed a pitch range of 0° to 20° from horizontal during operation will be effective. Therefore, as can be appreciated, pitch is not required. But as discussed, some pitch may promote beneficial operation.

Depth can also be selected according to desire or need. It is believed a depth range of 0 to 30 cm from soil surface will be effective. As can be seen, penetration into the soil is not required. But as discussed, there are reasons to get measurements below soil surface.

As can be appreciated, the soil opener 3, shank 2, and shank base 4 can be designed to have sufficient width to open a furrow sufficient for good soil to diamond contact and to carry and support the D-ATR-FTIR components, but minimize the width to reduce drag and disruption of the soil. The diameter of the surface of the diamond to contact the soil is a fraction of an inch. Therefore, a width on the order of the soil opening points or shank of the above-mentioned Orthman 6/DT (e.g. around 1-2 inches) is one form these components could take.

Materials

The materials for the components of tool 10 can vary. They need to be robust enough for the functions described. Likewise for the internal components of housing 5; the precise model numbers and specifications can vary so long as they meet the functions described above for them.

Diamond

Figure 21:
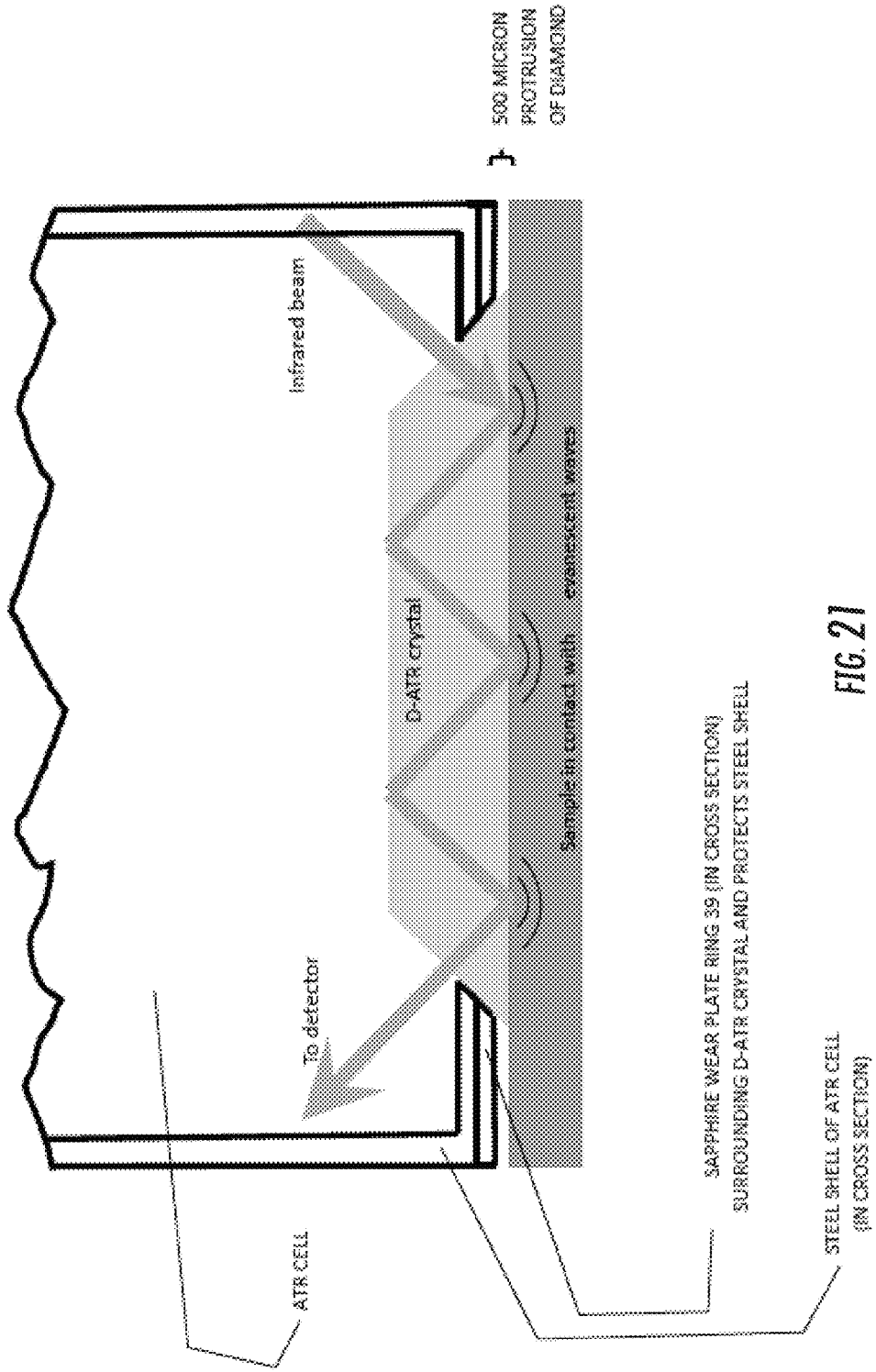
FIG. 21 is a highly diagrammatic view of the distal (ground contacting) portion of the D-ATR part of the exemplary embodiment showing how the diamond could protrude slightly and an optional wear plate (e.g. sapphire) around the diamond.

As illustrated, diamond 8 can be placed in the middle of the distal end of ATR cell 7. Diamond 8 can be relatively small (e.g. just a few centimeters in diameter). Its distal surface could be flush with the ATR surface that surrounds it and flush with the bottom of shank base 4. Alternatively, diamond 8 might be mounted so that its distal surface (the surface that is intended to contact the soil) protrudes slightly beyond the ATR and/or shank base 4. One example would be about 500 microns protrusion. This would promote soil-to-diamond contact. FIG. 21 illustrates schematically that slight protrusion (not to scale). Not only is diamond wear-resistant, it is transparent to the wavelengths of IR used here.

Optional Wear Plate (e.g. Sapphire)

An example of an option is to add a wear plate surrounding the diamond to protect the ATR cell from abrasion as the tool moves along soil, as previously mentioned. FIG. 21 also diagrammatically illustrates this option. Wear plate 39 can be attached in a variety of ways. Non-limiting examples would be by adhesive(s), press- or interference-fit, or some type of fastener(s) or retainer. One material for the wear plate is sapphire. It is quite durable and resistant to abrasion to protect the distal surface of the ATR cell from abrasion as the tool is moved through the soil. Sapphire may not be transparent to all the wavelengths relevant for this tool, but it does not have to be because spectra is acquired through diamond 8. Other materials are possible. The wear plate could be removably mounted so that it could be replaced over time.

One example of mounting the wear plate is to simply glue or adhere around the diamond. The diamond disc can also be mounted to the ATR cell by glue or adhesive. The opening in the middle of the wear plate can be drilled or otherwise fabricated so that the outside diameter or perimeter of the diamond is essentially flush with the inside diameter or perimeter of that opening on the wear plate. The wear plate can surround diamond and leave it exposed, but cover and protect the ATR or steel (or other material) that holds the diamond from abrasion. As will be appreciated, even steel will be abraded by the contemplated type of movement of the tool through agricultural field soil.

Data Acquisition and Processing

The techniques for communicating between components, and utilizing the nitrate predictions can vary according to need or desire. This includes how they are communicated and used to instruct operation of a fertilizer applicator. This can include both wired and wireless communications.

The specific diamond, ATR, and FTIR can vary, as can their operation and communication with a processor. The algorithms used to process and interpret the data can vary.

For example, instead of an FTIR spectrometer, a mid-IR spectrometer or a filter-based IR spectrometer might be used. Single reflection ATR technique can be used, but multiple reflection is possible. U.S. Pat. No. 8,933,406 to inventors Ressler et al. and U.S. Pat. No. 8,290,375 to inventors Szafraniec et al., each incorporated by reference herein, are patents owned by Agilent which give details about other examples of spectrometers or methods of acquiring spectra.

Chemometric techniques for processing the acquired spectra can vary. Some examples are given in the description above and FIG. 9. It is to be understood, however, that there can be a variety of approaches.

For example, it is presently contemplated that it will be sufficient and effective to simply use some technique to filter or throw out unusable spectra and then truncate the remaining spectra according to desire or need. One example of a filter is a least squares technique. Normalization and averaging are not required. However, they are given as possible additional data processing steps that the designer could consider.

Still further, as indicated, the present invention can be used as a stand-alone system in the sense it could be moved through a field and used to predict/estimate nitrate concentration. The predictions could be used as desired by the operator. For example, they could simply be used with the LSNT test for determining where and how much side dress nitrogen to apply.

It could be compiled and stored. The results could be studied at a later time. They could be used immediately, such as the example of modulating a side dress nitrogen applicator during the same pass as the nitrate concentration levels are being obtained.

But as can be appreciated by those skilled in the art, the present invention can complement other data relevant to the field or to the farmer. For example, the present invention could be used to supply nitrate concentration estimates to a processor or computer that can use it or integrate it with other information or data.

A few non-limiting examples are:
Climate models.
Soil-carbon-nitrogen cycle models.
Weather information (e.g. historical, present, or even future prediction).
Field information (slope, soil type,
Crop data (historical, present, or future).

These are but a few of the types of additional information or data that might be combined with the nitrate predictions according to the methods and systems of the present invention.

Likewise, nitrate level can be estimated, but the tool, method, and system could be configured and used to estimate other substances. A few non-limiting examples are soil moisture content and soil organic carbon content.

Motive Force

A typical motive force is a tractor which can navigate an agriculture field non-destructively of growing crops, and in particular, growing corn at or around the relevant LSNT (or similar test) time. Tool 10 could be carried on a pull-behind framework dedicated to tool 10 (similar to the approach of U.S. Pat. No. 8,204,689). Or it might be carried on the tractor. See also FIG. 20.

As indicated, functions such as electrical power, instrument control (including the IR spectrometer), data storage, data processing, and GPS data could be at the tractor. However, this does not preclude one or more of these functions to be at, near, or on the tool.

Alternatively, tool 10 could be added to an existing implement (including a conventional tool bar frame). The motive force would need to be able to pull or push such an implement with one or more tools 10. If used in the mode of also applying nitrogen fertilizer in the same pass, the motive force would need that the capability to pull or push that added function, which can include a number of ground-penetrating injection knives and a substantial container or tank.

Fertilizer Applicator

The fertilizer applicator can vary, as can the form in which nitrogen is added to the soil. As indicated, liquid nitrogen side dress may be a preferred method when used with a late spring application.

REFERENCES (EACH OF WHICH IS INCORPORATED BY REFERENCE IN ITS ENTIRETY HEREIN)

Agilent 4100 Exoscan FTIR Spectrometer. www.analytik.co.uk/portable-ftir-spectroscopy-4100-exosan.htm Bausch, W., K. Diker. 2001. Innovative Remote Sensing Techniques to Increase Nitrogen Use Efficiency of Corn. Commun. Soil Sci. Plant Anal. 32:1371-1390.

Blackmer, A., D. Pottker, M. Cerrato, and J. Webb. 1989. Correlations Between Soil Nitrate Concentrations in Late Spring and Corn Yields in Iowa. J. Prodc. Agric. 2:103-109.

Cassman, K., A. Dobermann, and D. Walters. 2002. Agro-ecosystems, N-Use Efficiency, and N Management. AMBIO: A Journal of the Human Environment. 31:132-140.

Chang, C. W., D. A. Laird, and C. J. Hurburgh. 2005. Influence of Soil Moisture on Near-Infrared Reflectance Spectroscopic Measurement of Soil Properties. Soil Sci. 170(4):244-255.

Chang, C. W., D. A. Laird, M. J. Mausbach, and C. J. Hurburgh. 2001. Near infrared reflectance spectroscopy-principal component regression analyses of soil properties. Soil Sci. Soc. Am. J. 65:480-490.

Chang, C. W. and D. A. Laird. 2002. NIRS analysis of soil C and N. Soil Sci. 167:110-116.

Christy, C., E. Lund, and D. A. Laird. 2003. Mapping Soil Carbon with On-The-Go Near Infrared Spectroscopy. In: Proc.CASMGS Carbon Measurement and Monitoring Forum, Kansas State University in Manhattan, Kans., October 15-17.

Christy, C. D., P. Drummond and D. A. Laird. 2003. An On-The-Go Spectral Reflectance Sensor for Soil. Paper No. 031044, p. 1-7. Proceedings of 2003 ASAE Annual International Meeting Sponsored by ASAE Riviera Hotel and Convention Center Las Vegas, Nev., USA 27-30 Jul. 2003.

Environmental Protection Agency. 2011. Reactive Nitrogen in the United States: An Analysis of Inputs, Flows, Consequences, and Management Options; EPA-SAB-11-013; EPA Science Advisory Board, U.S. Environmental Protection Agency: Washington, D C, 2011.

Graham, C. J., H. M. van Es, J. J. Melkonian, and D. A. Laird. 2011. Improved nitrogen and energy use efficiency using NIR estimated soil organic carbon and N simulation modeling. P 321-336. In: D. A. Clay and J. Shanahan. GIS Applications in Agriculture—Nutrient Management for Improved Energy Efficiency. CRC Press, Taylor and Francis Group, LLC.

Jaynes, D. B., D. L. Dinnes, D. W. Meek, D. L. Karlen, C. A. Cambardella, T. S. Colvin. 2004. Using the Late Spring Nitrate Test to Reduce Nitrate Loss within a Watershed. J. Environ. Qual. 33:669-677.

Jones, R. W., S. J. Rathke, D. A. Laird, and J. F. McClelland. 2013. Real-Time Sensing of Soil Nitrate Concentration in the Parts per Million Range while the Soil is in Motion. Applied Spectroscopy. 67:1106-1110.

Linker, R., A. Kenny, A. Shaviv, L. Singher, and I. Shmulevich. 2004. Fourier Transform Infrared-Attenuated Total Reflection Nitrate Determination of Soil Pastes Using Principal Component Regression, Partial Least Squares, and Cross-Correlation. Appl. Spectrosc., 2004, 58, 516-520.

Linker, R., I. Shmulevich, A. Kenny, and A. Shaviv. 2005. Soil identification and chemometrics for direct determination of nitrate in soils using FTIR-ATR mid-infrared spectroscopy. Chemosphere 61: 652-658.

Magdoff, F., W. Jokela, R. Fox, and G. Griffin. 1990. A Soil Test for Nitrogen Availability in the Northeastern United States. Commun. Soil Sci. Plant Anal. 21:1103-1115.

Magdoff, F. 1991. Understanding the Magdoff Pre-Sidedress Nitrate Test for Corn. J. Production Agric., 4:297-305.

Meisinger, J. 1984. Evaluating Plant-Available Nitrogen in Soil-Crop Systems. In Nitrogen in Crop Production; R.

Meisinger, J. 1984. Evaluating Plant-Available Nitrogen in Soil-Crop Systems. In Nitrogen in Crop Production; R. D. Hauck, Ed.; ASA, SSSS, CSSA: Madison, Wis., 1984; 391-416.

National Academy of Engineers. 2014. NAE Grand Challenges for Engineering: Manage the Nitrogen Cycle. www.engineeringchallenges.org/ems/8996/9132.aspx, Stoner, N. 2011. Working in Partnership with States to Address Phosphorus and Nitrogen Pollution through Use of a Framework for State Nutrient Reductions. Memorandum, Mar. 16, 2011. Office of Water, United States Environmental Protection Agency. 6 p.

Thermo Scientific TruDefender FT. www.ahurascientific.com/chemical-explosives-id/products/trudefenderft/

Vagts, T. 2014. Utilizing the Late Spring Nitrate Test to Optimize Nitrogen Use and Corn Grain Yields. www.extension.iastate.edu/nwcrops/LSNT.htm (web site checked 5-16-14).

What is claimed is:

1. A system for estimating nitrate levels in soil in a field comprising:
    a. a motive force that can be moved through a field;
    b. a soil sensing tool that can be moved through a field by the motive force comprising:
        i. a shank having a soil cutting leading edge and a trailing tail with a ground-contacting side;
        ii. a housing mounted on the tail;
        iii. an infrared (IR) spectrometer in the housing;
        iv. an attenuated total internal reflectance (ATR) cell operatively mounted on the IR spectrometer, the ATR cell having an exposed optical surface in the ground contacting side of the trailing tail for direct contact with soil when the shank is at soil in a field;
        v. the optical surface of the ATR cell comprising a material that is transmissive of a range of spectra including spectra relevant to detecting $NO_3^-$ concentrations, wherein the material comprises diamond;
        vi. a closed path between the optical surface and the IR spectrometer; and
    c. a processor operatively connected to the IR spectrometer to process spectral data acquired from the diamond-based optical surface and ATR cell, filter spectral data related to acquired spectra irrelevant to estimating $NO_3^-$ and derive a prediction of nitrate level.

2. The system of claim 1 wherein the IR spectrometer comprises one of:
    a. a Fourier transform infrared (FTIR) spectrometer;
    b. a mid-IR spectrometer; and
    a filter-based IR spectrometer.

3. The system of claim 1 wherein the spectral data is evaluated relative to late spring nitrate test (LSNT) including by obtaining spectra readings from plural depths in soil.

4. The system of claim 1 wherein the processor includes software which:
    a. filters acquired spectral data to reject unacceptable spectra; and/or
    b. truncates the filtered spectra data to an optimized wavenumber range.

5. The system of claim 1 further comprising:
    a. a georeferencing component operatively connected to the processor to correlate a georeference with spatially-resolved predictions of nitrate level; and
    b. a digital memory to store the correlated georeferenced nitrate level predictions for use by a nitrogen fertilizer applicator adapted to modulate nitrogen fertilizer application based on the georeferenced predictions of nitrate level either:
        i. immediately; or
        ii. in a later second pass through the field.

6. The system of claim 1 further comprising a global positioning system (GPS) in operative connection to the processor.

7. The system of claim 1 further comprising a nitrogen fertilizer applicator in operative connection with the processor.

8. The system of claim 1 further comprising an interface with the shank which adjusts the plane defined by the optical surface of the diamond ATR cell with respect to the soil surface for at least one of:
    a. pitch; and
    b. depth.

9. The system of claim 8 wherein pitch is adjustable between approximately 0 and 20 degrees relative to an averaged soil surface level.

10. The system of claim 8 wherein depth is adjusted approximately 0 to 30 cm relative to soil surface.

11. An apparatus for sensing chemical concentration levels while being moved through a field comprising:
    a. a shank having a soil cutting leading edge and a trailing tail with a ground-contacting side;
    b. a housing mounted on the tail;
    c. an attenuated total reflectance (ATR) cell in the housing, the ATR cell having an exposed optical surface in the ground contacting side of the trailing tail for direct contact with soil when the shank is at soil in a field and defining an enclosed optical path from the optical surface on the ground contacting side through the ATR cell to a connector adapted for operative connection to an IR spectrometer;
    d. the optical surface of the ATR cell comprising diamond;
    at least one actuator to adjust one or more of pitch and depth of the ground-contacting side of the shank relative to a field.

12. The apparatus of claim 11 wherein the at least one actuators to adjust pitch and/or depth comprises:
   a. a hydraulic mechanism;
   b. mechanical mechanism; or
   c. an electromechanical mechanism.

13. The apparatus of claim 11 wherein the shank comprises:
   a. a leading edge of hardened steel extending forwardly;
   b. a trailing edge extending rearwardly from the leading edge with the ground-contacting side being relatively flat and widened relative the leading edge.

14. The apparatus of claim 11 further comprising an IR spectrometer mounted in the housing via vibration and shock absorbing means and at least substantially protected from external environment including moisture, dust and debris.

15. The apparatus of claim 1 wherein the apparatus comprises plural said hanks, the ground-contacting side of each said shank offset relative to one another vertically when at soil for different depth measurements in soil.

16. The apparatus of claim 11 in operative connection to a global positioning system (GPS) unit.

17. The apparatus of claim 11 in operative connection to a processor or computer including algorithms to evaluate spectra produced by the IR spectrometer relative to a selected chemical concentration level.

18. The apparatus of claim 17 wherein the chemical concentration and algorithms relate to a nitrate level.

19. The apparatus of claim 17 wherein the chemical concentration and the algorithms relate to nitrate level and one or more of:
   a. late spring nitrate test (LSNT) factors;
   b. calibration libraries;
   c. pre-sidedress nitrate test (PSNT) factors.

20. The apparatus of claim 18 in combination with a sidedress nitrogen fertilizer applicator so that estimated nitrate levels can be used to modulate the fertilizer applicator while moving in a field.

21. The apparatus of claim 1 further comprising:
   a. an electrical power supply available to the IR spectrometer and processor.

22. The apparatus of claim 1 further comprising:
   a. a georeferencing component automatically supplying the processor with georeferencing data when moving through a field;
   b. a nitrate level digital map of a field or portion of a field with the georeferencing data correlated with the nitrate level estimates; and
   c. a fertilizer applicator to apply fertilizer to the field based on the nitrate level digital map.

* * * * *

UNITED STATES PATENT AND TRADEMARK OFFICE
CERTIFICATE OF CORRECTION

| | |
|---|---|
| PATENT NO. | : 10,345,283 B1 |
| APPLICATION NO. | : 15/372066 |
| DATED | : July 9, 2019 |
| INVENTOR(S) | : David Laird, Natalia Rogovska and Chien-Ping Chiou |

Page 1 of 1

It is certified that error appears in the above-identified patent and that said Letters Patent is hereby corrected as shown below:

In the Claims

In Column 27, Claim 1, Line 65:
DELETE "$NO_3^-$" after "detecting"
INSERT --$NO_3^-$-- after "detecting"

In Column 28, Claim 1, Line 7:
DELETE "$NO_3^-$" before "and"
INSERT --$NO_3^-$-- before "and"

In Column 29, Claim 12, Line 2:
DELETE "actuators" before "to"
INSERT --actuator-- before "to"

In Column 29, Claim 12, Line 4:
INSERT --a-- before the word "mechanical"

Signed and Sealed this
Fifth Day of November, 2019

Andrei Iancu
*Director of the United States Patent and Trademark Office*